(12) United States Patent
Gobbi et al.

(10) Patent No.: US 8,791,163 B2
(45) Date of Patent: Jul. 29, 2014

(54) MELATONIN LIGANDS HAVING ANTIDEPRESSANT ACTIVITY AS WELL AS SLEEP INDUCING PROPERTIES

(75) Inventors: Gabriella Gobbi, Montreal (CA); Marco Mor, Ghedi (IT); Silvia Rivara, Noceto (IT); Franco Fraschini, Milan (IT); Giorgio Tarzia, Petriano (IT); Annalida Bedini, Urbino (IT); Gilberto Spadoni, Urbino (IT); Valeria Lucini, Milan (IT)

(73) Assignees: McGill University, Montreal (CA); Universita Degli Studi di Parma, Parma (IT); Universita Degli Studi di Milano, Milan (IT); Universita Degli Studi di Urbino, Urbino (IT)

( * ) Notice: Subject to any disclaimer, the term of this patent is extended or adjusted under 35 U.S.C. 154(b) by 1408 days.

(21) Appl. No.: 12/160,728

(22) PCT Filed: Jan. 12, 2007

(86) PCT No.: PCT/CA2007/000055
§ 371 (c)(1),
(2), (4) Date: Jun. 8, 2010

(87) PCT Pub. No.: WO2007/079593
PCT Pub. Date: Jul. 19, 2007

(65) Prior Publication Data
US 2010/0267836 A1    Oct. 21, 2010

Related U.S. Application Data

(60) Provisional application No. 60/758,531, filed on Jan. 13, 2006, provisional application No. 60/822,730, filed on Aug. 17, 2006.

(51) Int. Cl.
    A61K 31/16    (2006.01)
    C07C 233/00   (2006.01)
    C07C 233/35   (2006.01)

(52) U.S. Cl.
    USPC .......................................... 514/630; 564/220

(58) Field of Classification Search
    None
    See application file for complete search history.

(56) References Cited

U.S. PATENT DOCUMENTS

| 3,869,442 A |   | 3/1975  | Weaver et al. ............. 260/207.1 |
| 4,260,679 A | * | 4/1981  | Tsuda et al. ..................... 435/10 |
| 6,150,415 A |   | 11/2000 | Hammock et al. ............ 514/588 |

FOREIGN PATENT DOCUMENTS

| EP | 0 706 994  | 4/1996  |
| JP | 60-241899  | 11/1985 |

OTHER PUBLICATIONS

Bent et al., "Chemical constitution, electrochemical, photographic and allergenic properties of p-amino-n-dialkylanilines," Communication No. 1385 from the Kodak Research Laboratories, J. Am. Chem. Soc., 73(7):3100-3125, 1951.
Orelli et al., "Synthesis and properties of 1-aryl-2-alkyl-1,4,5,6-tetrahydrophyrimidines," J. Heterocyclic Chem., 36:105-112, 1999.

\* cited by examiner

Primary Examiner — Sreeni Padmanabhan
Assistant Examiner — Jody Karol
(74) Attorney, Agent, or Firm — Fulbright & Jaworski LLP

(57) ABSTRACT

Novel melatonin ligands of Formula I:

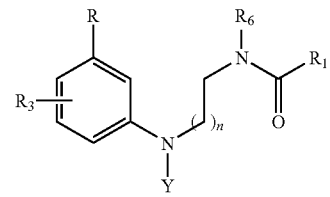

or pharmaceutically acceptable salts thereof wherein: n is 1 or 2; m is 0, 1 or 2; p is 0, 1, 2, 3, 4, 5, 6, 7 or 8; v is 2 or 3; A is aryl or heteroaryl; Z is O, S or $NR_8$; Y is selected from the group consisting of hydrogen, aryl, heteroaryl, $C_1$-$C_6$ alkyl, $C_3$-$C_6$ cycloalkyl, and

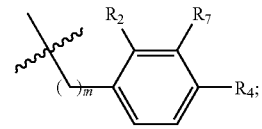

R is selected from the group consisting of hydrogen, hydroxyl, —$OCF_3$, $CF_3$, $C_1$-$C_8$ alkyl, $C_1$-$C_8$ alkyloxy, $C_1$-$C_8$ alkylthio, halogen and —Z—$(CH_2)_p$-A; $R_1$ is selected from the group consisting of $C_1$-$C_4$ alkyl, $C_3$-$C_6$ cycloalkyl, $CF_3$, hydroxy-substituted $C_1$-$C_4$ alkyl, hydroxy-substituted $C_3$-$C_8$ cycloalkyl, and $NHR_5$, wherein $R_5$ is $C_1$-$C_3$ alkyl or $C_3$-$C_6$ cycloalkyl; $R_2$ is selected from the group consisting of: hydrogen, $C_1$-$C_4$ alkyl, $C_1$-$C_4$ alkyloxy, $OCF_3$, $CF_3$, hydroxyl, and halogen; $R_3$ is selected from the group consisting of hydrogen, $C_1$-$C_4$ alkyl, $C_1$-$C_4$ alkyloxy, $OCF_3$, $CF_3$, hydroxyl, and halogen; R and $R_3$ may be connected together to form an —O—$(CH_2)_v$ bridge representing with the carbon atoms to which they are attached a 5- or 6-membered heterocyclic ring system; $R_4$ is selected from the group consisting of hydrogen, $C_1$-$C_4$ alkyl, $C_1$-$C_4$ alkyloxy, $OCF_3$, $CF_3$, hydroxyl, and halogen; $R_6$ is selected from the group consisting of hydrogen and $C_1$-$C_6$ alkyl; $R_7$ is selected from the group consisting of hydrogen, $C_1$-$C_4$ alkyl, $C_1$-$C_4$ alkyloxy, $OCF_3$, $CF_3$, hydroxyl, and halogen; and $R_8$ is selected from the group consisting of hydrogen and $C_1$-$C_4$ alkyl.

26 Claims, 10 Drawing Sheets

MELATONIN LIGANDS HAVING ANTIDEPRESSANT ACTIVITY AS WELL AS SLEEP INDUCING PROPERTIES

CROSS REFERENCE TO RELATED APPLICATIONS

This application is a national phase application under 35 U.S.C. §371 of International Patent Application PCT Application No. PCT/CA2007/000055, filed 12 Jan. 2007, which claims the benefit of U.S. Provisional Application 60/758,531 filed 13 Jan. 2006 and U.S. Provisional Application 60/822,730 filed 17 Aug. 2006. The entire contents of these applications are incorporated by reference.

FIELD OF THE INVENTION

The present invention relates to novel melatonin ligands having antidepressant activity as well as sleep inducing properties.

BACKGROUND OF THE INVENTION

Melatonin (N-acetyl-5-methoxytryptamine, MLT) is a neurohormone, primarily secreted at night in all species by the pineal gland (Barrenetxe, J.; Delagrange, P.; Martinez, J. A. *J. Physiol. and Biochem.* 2004, 60, 61-72).

The circadian pattern of MLT secretion, coupled with the localization of specific MLT binding sites in the brain region associated with the "biological clock", suggests that MLT may play an important role in modulation of the sleep-wake cycle and circadian rhythms in humans (Pevet, P.; Bothorel, B.; Slotten, H.; Saboureau, M. *Cell Tissue Res.* 2002, 309, 183).

There is evidence that the administration of MLT is of clinical utility in the treatment of various conditions including jet-lag, work-shift syndrome, sleep disorders, glaucoma, reproduction, cancer, immune disorders, obesity, eating disorders, and other neuroendocrine disorders, neurodegenerative disorders, cardiovascular diseases, neuropsychiatric diseases such as depression, anxiety, Alzheimer's disease, Parkinson's disease and other motor related diseases, autism, attention deficit hyperactivity disorder and some inflammatory diseases such as rheumatoid arthritis.

The chronobiotic properties of MLT are of particular interest since the disorganization of internal rhythms is believed to be involved in the pathophysiology of depression. Melatonin was suggested as having therapeutic benefits for individuals suffering from depression (Halbreich, U. *Psychopharmacol. Bull.* 1997, 33, 281-286; Eison, A. S.; Freeman, R. P.; Guss, V. B.; Mullins, U. L.; Wright, R. N. *J. Pharmacol. Exp. Ther.* 1995, 273, 304-308; Brotto, L. A.; Barr, A. M.; Gorzalka, B. B. *Eur. J. Pharmacol.* 2000, 402, 87-93). Moreover, some melatonin agonists having improved properties in comparison to melatonin are now in clinical trials for the treatment of depression, insomnia or circadian rhythm sleep disorders (Loo, H.; Hale, A.; D'haenen, H. *Int. Clin. Psychopharmacol.* 2002, 17, 239-47; Turek, F. W; Gillette, M. U. *Sleep Med.* 2004, 5, 523-32; Chilman-Blair, K.; Castaner, J.; Bayes, M.; Silvestre, J. S.; Bayes, M. *Drug Future* 2003, 28, 950; Zemlan, F. P.; Mulchahey, J. J.; Scharf, M. B.; Mayleben, D. W.; Rosenberg, R.; Lankford, A. *J. Clinic. Psychiatry* 2005, 66, 384-390). Furthermore, the treatment of stressed mice with MLT was shown to reverse some stress-induced behavioral disturbances (Kopp, C.; Vogel, E.; Rettori, M.-C.; Delagrange, P.; Misslin, R. *Behaviour Pharmacol.* 1999, 10, 73).

Most of the physiological effects of MLT result from the activation of high-affinity G-protein coupled receptors, two of which ($MT_1$ and $MT_2$) have been found in mammals including humans and which have been subsequently cloned (Reppert, S. M.; Weaver, D. R.; Goodson, C. *Trends Pharmacol. Sci.* 1996, 17, 100; Dubocovich, M. L.; Cardinali, D. P.; Delagrange, P.; Krause, D. N.; Strosberg, A. D.; Sugden, D.; Yocca, F. D. The IUPHAR compendium of receptor characterization and classification. *IUPHAR Media, London;* 2000, pp 271-277; Von Gall, C.; Stehle, J. H.; Weaver, D. R. *Cell Tissue Res.* 2002, 309, 151). A third subtype ($Mel_{1c}$), first cloned from *Xenopus laevis*, has been found in non-mammalians only.

In addition to these high-affinity MLT receptors ($K_i \cong 0.1$ nM), another low-affinity MLT binding site, termed $MT_3$ ($K_i \cong 60$ nM), has recently been characterized as a melatonin-sensitive form of the human enzyme quinone reductase 2 (Nosjean O., Ferro M., Cogé F., Beauverger P., Henlin J.-M., Lefoulon F., Fauchére J.-L., Delagrange P., Canet E., Boutin J. A. *J. Biol. Chem.* 2000, 275, 31311).

Other effects of MLT described in the literature include its neuroprotective (Liu, R. Y.; Zhou, J. N.; van Heerikhuize, J; Hofman, M. A.; Swaab, D. F. *J. Clin. Endocrinol. Metab.* 1999, 84, 323-327; Zisapel, N. *Cellular and Molecular Neurobiology* 2001, 21, 605-14; Kondoh, T.; Uneyama, H.; Nishino, H.; Torii, K. *Life Sci.* 2002, 72, 583-90), anti-inflammatory (Genovese, T.; Mazzon, E.; Muia, C.; Bramanti, P.; De Sarro, A.; Cuzzocrea, S. *J. Pineal Res.* 2005, 38, 198-208; Maestroni, G. J. M.; Sulli, A.; Pizzorni, C.; Villaggio, B.; Cutolo, M. *Ann. N.Y. Acad. Sci.* 2002, 966, 271-275), pain modulatory (Peres, M. F. *Cephalalgia.* 2005, 25, 403-11), retinal (Iuvone, P. M.; Tosini, G.; Pozdeyev, N.; Hague, R.; Klein, D. C.; Chaurasia, S. S. *Progress in Retinal and Eye Research* 2005, 24, 433-456), vascular (Sewerynek, E. *Neuroendocrinology Letters* 2002, 23 (Suppl. 1), 79-83; Doolen, S.; Krause, D. N.; Dubocovich, M. L.; Duckles, S. P. *Eur. J. Pharmacol.* 1998, 345, 67-69; Cagnacci, A.; Arangino, S.; Angiolucci, M.; Maschio, E.; Longu, G.; Melis, G. B. *J. Pineal Res.* 1997, 22, 16-19), antitumor ((a) Blask, D. E.; Sauer, L. A.; Dauchy, R. T. *Curr. Topics in Med. Chem.* 2002, 2, 113-132; (b) Sauer, L. A.; Dauchy, R. T.; Blask, D. E. *Life Sci.* 2001, 68, 2835-2844; (c) Collins, A.; Yuan, L.; Kiefer, T. L.; Cheng, Q.; Lai, L.; Hill, S. M. *Cancer Lett.* 2003, 189, 49-57), and antioxidant (Sofic, E.; Rimpapa, Z.; Kundurovic, Z.; Sapcanin, A.; Tahirovic, I.; Rustembegovic, A.; Cao, G. *J. Neural Transmission* 2005, 112, 349-358) properties.

Finally, a significant increase in the serum melatonin mean level could be observed in severely obese women (Shafii, M; MacMillan, D. R.; Key, M. P.; Kaufman, N.; Nahinsky, I. D. *J. Am. Acad. Child Adolesc. Psychiatry* 1997, 36, 412-6) suggesting a possible use of melatonin ligands in the treatment of obesity (Bylesjo, E. I.; Boman, K.; Wetterberg, L. *Int. J. Eat Disord.* 1996, 20, 443-46).

The specification refers to a number of documents, the contents of which is herein incorporated by reference in their entirety.

SUMMARY OF THE INVENTION

The present invention relates to novel melatonin ligands having antidepressant activity as well as sleep inducing properties. The present invention also relates to therapeutic compositions comprising such novel melatonin ligands or pharmaceutically acceptable salts thereof for the treatment of depression and sleep disorders.

In an embodiment, the present invention relates to a compound of Formula I:

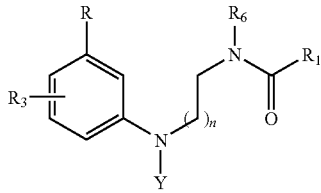

Formula I or a pharmaceutically acceptable salt thereof, wherein:
n is 1 or 2;
m is 0, 1 or 2;
p is 0, 1, 2, 3, 4, 5, 6, 7 or 8;
v is 2 or 3;
A is aryl or heteroaryl;
Z is O, S or $NR_8$;
Y is selected from the group consisting of hydrogen, aryl, heteroaryl, $C_1$-$C_6$ alkyl, $C_3$-$C_6$ cycloalkyl, and

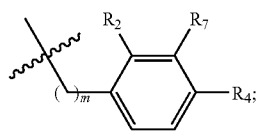

R is selected from the group consisting of hydrogen, hydroxyl, —$OCF_3$, $CF_3$, $C_1$-$C_8$ alkyl, $C_1$-$C_8$ alkyloxy, $C_1$-$C_8$ alkylthio, halogen and —Z—$(CH_2)_p$-A;
$R_1$ is selected from the group consisting of: $C_1$-$C_4$ alkyl, $C_3$-$C_6$ cycloalkyl, $CF_3$, hydroxy-substituted $C_1$-$C_4$ alkyl, hydroxy-substituted $C_3$-$C_6$ cycloalkyl, and $NHR_5$, wherein $R_5$ is $C_1$-$C_3$ alkyl or $C_3$-$C_6$ cycloalkyl;
$R_2$ is selected from the group consisting of: hydrogen, $C_1$-$C_4$ alkyl, $C_1$-$C_4$ alkyloxy, $OCF_3$, $CF_3$, hydroxyl, and halogen;
$R_3$ is selected from the group consisting of hydrogen, $C_1$-$C_4$ alkyl, $C_1$-$C_4$ alkyloxy, $OCF_3$, $CF_3$, hydroxyl, and halogen;
R and $R_3$ may be connected together to form an —O—$(CH_2)_v$— bridge representing with the carbon atoms to which they are attached a 5- or 6-membered heterocyclic ring system;
$R_4$ is selected from the group consisting of hydrogen, $C_1$-$C_4$ alkyl, $C_1$-$C_4$ alkyloxy, $OCF_3$, $CF_3$, hydroxyl, and halogen;
$R_6$ is selected from the group consisting of hydrogen and $C_1$-$C_6$ alkyl;
$R_7$ is selected from the group consisting of hydrogen, $C_1$-$C_4$ alkyl, $C_1$-$C_4$ alkyloxy, $OCF_3$, $CF_3$, hydroxyl, and halogen; and
$R_8$ is selected from the group consisting of hydrogen and $C_1$-$C_4$ alkyl.

In an embodiment, the present invention relates to novel melatonin ligands having antidepressant activity as well as sleep inducing properties, the compounds being ligands to MLT receptor subtypes $MT_1$ and or $MT_2$.

In an embodiment, the present invention relates to compounds selected from the group consisting of N-[2-(diphenylamino)ethyl]acetamide, N-{2-[(3-Methoxyphenyl)-phenylamino]ethyl}acetamide, N-[2-(bis-3-methoxyphenylamino)ethyl]acetamide, N-{2-[(4-Methoxyphenyl)-3-methoxyphenylamino]ethyl}acetamide, N-{2-[(4-Methoxyphenyl)-phenylamino]ethyl}acetamide, N-{2-[(3-bromophenyl)-phenylamino]ethyl}acetamide, N-{2-[(3-Methoxyphenyl)-β-naphthylamino]ethyl}acetamide, N-{2-[(3-phenylbutoxyphenyl)-phenylamino]ethyl}acetamide, N-{2-[(3-Methoxyphenyl)-methylamino]ethyl}acetamide, N-{2-[(3-Methoxyphenyl)-benzylamino]ethyl}acetamide, N-{2-[(3-Methoxyphenyl)-amino]ethyl}acetamide, N-{3-[(3-Methoxyphenyl)-methylamino]propyl}acetamide, N-{2-[(3-Methoxyphenyl)-phenylamino]ethyl}butanamide, N-{2-[(3-Methoxyphenyl)-phenylamino]ethyl}cyclobutancarboxamide, N-Methyl-N-{2-[(3-methoxyphenyl)-phenylamino]ethyl}acetamide; N-{2-[(3-Butoxyphenyl)-methylamino]ethyl}acetamide; N-{2-[(3-Hexyloxyphenyl)-methylamino]ethyl}acetamide, and N-{2-{[3-(4-phenylbutoxy)phenyl)-methylamino]}ethyl}acetamide.

In yet a further embodiment, the present invention relates to therapeutically effective compositions for treating a condition mediated by the $MT_1$ and/or $MT_2$ receptor, the compositions comprising one or more pharmaceutically acceptable excipients and a compound of Formula I or a pharmaceutically acceptable salt thereof.

In yet a further embodiment, the present invention relates to therapeutically effective compositions for treating a condition mediated by the $MT_1$ and/or $MT_2$ receptor, the compositions comprising one or more pharmaceutically acceptable excipients and a compound selected from the group consisting of N-[2-(diphenylamino)ethyl]acetamide, N-{2-[(3-Methoxyphenyl)-phenylamino]ethyl}acetamide, N-[2-(bis-3-methoxyphenylamino)ethyl]acetamide, N-{2-[(4-Methoxyphenyl)-3-methoxyphenylamino]ethyl}acetamide, N-{2-[(4-Methoxyphenyl)-phenylamino]ethyl}acetamide, N-{2-[(3-bromophenyl)-phenylamino]ethyl}acetamide, N-{2-[(3-Methoxyphenyl)-β-naphthylamino]ethyl}acetamide, N-{2-[(3-phenylbutoxyphenyl)-phenylamino]ethyl}acetamide, N-{2-[(3-Methoxyphenyl)-methylamino]ethyl}acetamide, N-{2-[(3-Methoxyphenyl)-benzylamino]ethyl}acetamide, N-{2-[(3-Methoxyphenyl)-amino]ethyl}acetamide, N-{3-[(3-Methoxyphenyl)-methylamino]propyl}acetamide, N-{2-[(3-Methoxyphenyl)-phenylamino]ethyl}butanamide, N-{2-[(3-Methoxyphenyl)-phenylamino]ethyl}cyclobutancarboxamide, N-Methyl-N-{2-[(3-methoxyphenyl)-phenylamino]ethyl}acetamide; N-{2-[(3-Butoxyphenyl)-methylamino]ethyl}acetamide; N-{2-[(3-Hexyloxyphenyl)-methylamino]ethyl}acetamide, and N-{2-[(3-(4-phenylbutoxy)phenyl)-methylamino]ethyl}acetamide.

In yet a further embodiment, the present invention relates to the treatment of sleep disorders, anxiety, depression, chronobiological disorders, as well as other conditions influenced by melatonin activity.

In yet a further embodiment, the present invention relates to pharmaceutical compositions comprising a therapeutically effective amount of one or more compounds of Formula I or pharmaceutically acceptable salts thereof, and at least one pharmaceutically acceptable excipient, non-limiting examples of which are carriers and diluents.

In yet a further embodiment, the present invention relates to pharmaceutical compositions comprising a pharmaceutically acceptable excipient and a compound selected from the group consisting of N-[2-(diphenylamino)ethyl]acetamide, N-{2-[(3-Methoxyphenyl)-phenylamino]ethyl}acetamide, N-[2-(bis-3-methoxyphenylamino)ethyl]acetamide, N-{2-[(4-Methoxyphenyl)-3-methoxyphenylamino]ethyl}acetamide, N-{2-[(4-Methoxyphenyl)-phenylamino]ethyl}acetamide, N-{2-[(3-bromophenyl)-phenylamino]ethyl}acetamide, N-{2-[(3-Methoxyphenyl)-β- naphthylamino]ethyl}acetamide, N-{2-[(3-phenylbutoxyphenyl)-phenylamino]ethyl}acetamide, N-{2-[(3-Methoxyphenyl)-methylamino]ethyl}acetamide, N-{2-[(3-Methoxyphenyl)-benzylamino]ethyl}acetamide, N-{2-[(3-Methoxyphenyl)-amino]ethyl}acetamide, N-{3-[(3-Methoxyphenyl)-methylamino]propyl}acetamide, N-{2-[(3-Methoxyphenyl)-phenylamino]ethyl}butanamide, N-{2-[(3-Methoxyphenyl)-phenylamino]ethyl}cyclobutancarboxamide, N-Methyl-N-{2-[(3-methoxyphenyl)-phenylamino]ethyl}acetamide; N-{2-[(3-Butoxyphenyl)-methylamino]ethyl}acetamide; N-{2-[(3-Hexyloxyphenyl)-methylamino]ethyl}acetamide, and N-{2-{[3-(4-phenylbutoxy)phenyl)-methylamino]}ethyl}acetamide.

Moreover, the present invention relates to a method of interacting with the $MT_1$ and/or $MT_2$ MLT receptor subtypes comprising administering to a subject in need thereof an effective amount of a compound of Formula I.

Finally, the present invention relates to a method of interacting with the $MT_1$ and/or $MT_2$ MLT receptor subtypes comprising administering to a subject in need thereof an effective amount of a compound selected from the group consisting of N-[2-(diphenylamino)ethyl]acetamide, N-{2-[(3-Methoxyphenyl)-phenylamino]ethyl}acetamide, N-[2-(bis-3-methoxyphenylamino)ethyl]acetamide, N-{2-[(4-Methoxyphenyl)-3-methoxyphenylamino]ethyl}acetamide, N-{2-[(4-Methoxyphenyl)-phenylamino]ethyl}acetamide, N-{2-[(3-bromophenyl)-phenylamino]ethyl}acetamide, N-{2-[(3-Methoxyphenyl)-β-naphthylamino]ethyl}acetamide, N-{2-[(3-phenylbutoxyphenyl)-phenylamino]ethyl}acetamide, N-{2-[(3-Methoxyphenyl)-methylamino]ethyl}acetamide, N-{2-[(3-Methoxyphenyl)-benzylamino]ethyl}acetamide, N-{2-[(3-Methoxyphenyl)-amino]ethyl}acetamide, N-{3-[(3-Methoxyphenyl)-methylamino]propyl}acetamide, N-{2-[(3-Methoxyphenyl)-phenylamino]ethyl}butanamide, N-{2-[(3-Methoxyphenyl)-phenylamino]ethyl}cyclobutancarboxamide, N-Methyl-N-{2-[(3-methoxyphenyl)-phenylamino]ethyl}acetamide; N-{2-[(3-Butoxyphenyl)-methylamino]ethyl}acetamide; N-{2-[(3-Hexyloxyphenyl)-methylamino]ethyl}acetamide, and N-{2-{[3-(4-phenylbutoxy)phenyl)-methylamino]}ethyl}acetamide.

Other objects, features and advantages of the present invention will become apparent from the following detailed description. It should be understood, however, that the detailed description and the specific examples, while indicating illustrative embodiments of the invention, are given by way of illustration only, since various changes and modifications within the spirit and scope of the invention will become apparent to those skilled in the art from this detailed description.

BRIEF DESCRIPTION OF THE DRAWINGS

Having thus generally described the invention, reference will now be made to the accompanying drawings, showing by way of illustration a preferred embodiment thereof, and in which.

DETAILED DESCRIPTION OF ILLUSTRATIVE EMBODIMENTS

Figure 1:
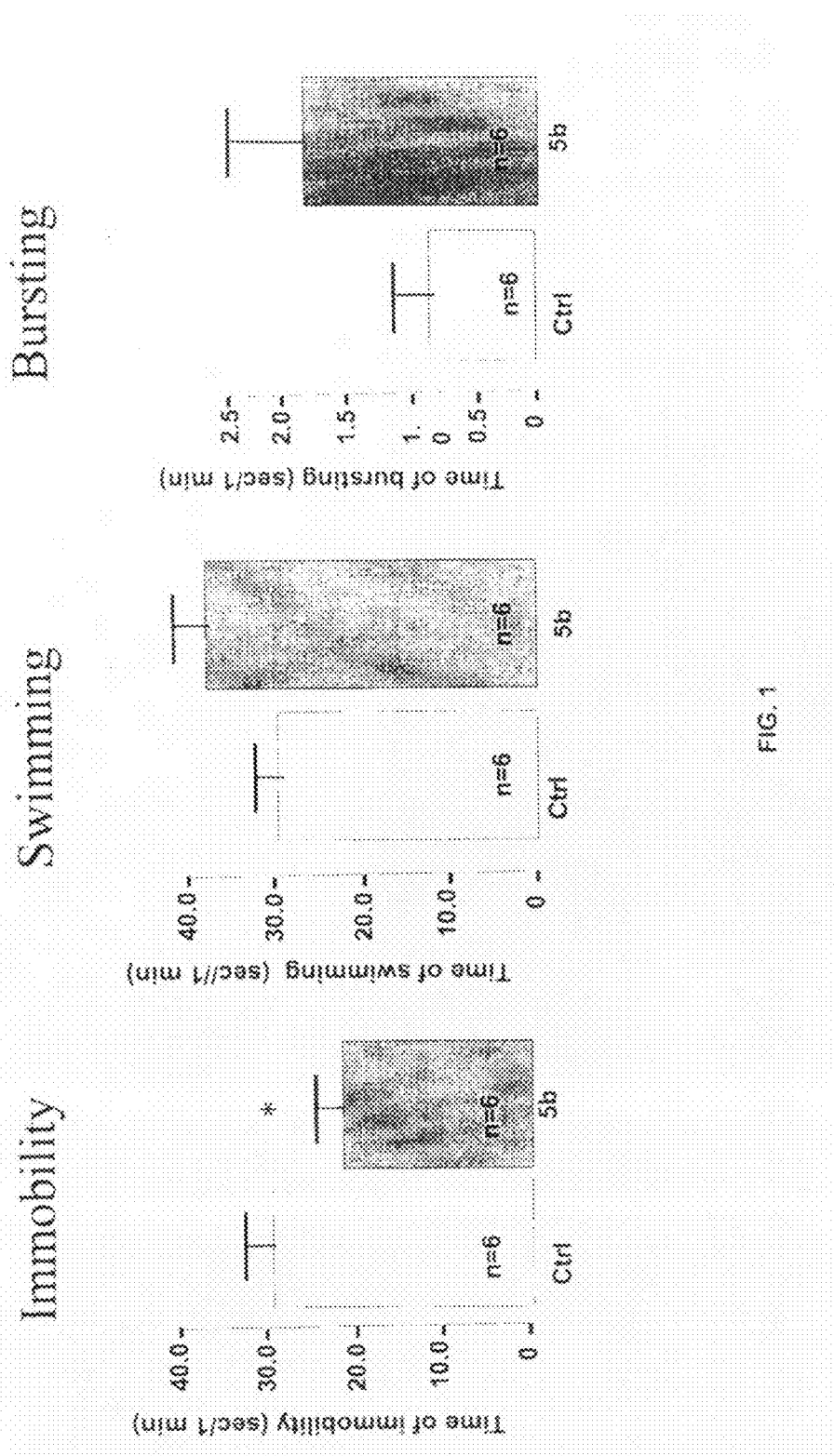
FIG. 1 shows the results obtained with the Forced Swim Test; a test for measuring depression-like behavior. Pretreatment with compound 5b (40 mg/kg; 24, 5 and 1 hour prior to the test; grey bars) decreased the immobility (*, p<0.05, Student t test), increased the tendency to swim, and increased the tendency to climb or burst. The decrease in immobility is an index of anti-depressant-like activity. Control animals (Ctrl, white bars) are treated with vehicle (DMSO/saline 7:3). Six animals per group were tested.

In order to provide a clear and consistent understanding of the terms used in the present specification, a number of definitions are provided below. Moreover, the present description refers to a number of routinely used chemical terms; definitions of selected terms are provided for clarity and consistency.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or method steps.

The term "about" is used to indicate that a value includes an inherent variation of error for the device or the method being employed to determine the value.

The term "$C_1$-$C_8$ alkyl", as used herein, is understood as being straight chain or branched chain alkyl groups non-limiting examples of which include methyl, ethyl, propyl, isopropyl, n-butyl, isobutyl, t-butyl, amyl, hexyl, heptyl and octyl.

The term "$C_1$-$C_8$ alkyloxy", as used herein, is understood as being straight chain or branched chain alkyloxy groups, non-limiting examples of which include methoxy, ethoxy, propoxy, isopropoxy, n-butoxy, isobutoxy and t-butoxy.

The term "halogen", as used herein, is understood as including fluorine, chlorine, bromine and iodine.

The term "$C_3$-$C_6$ cycloalkyl", as used herein, is understood as being a carbon-based ring system, non-limiting examples of which include cyclopropyl, cyclobutyl, cyclopentyl and cyclohexyl.

The term "aryl", as used herein, is understood as being an aromatic substituent which is a single ring or multiple rings fused together and which may optionally be substituted. When formed of multiple rings, at least one of the constituent rings is aromatic. In an embodiment, aryl substituents include phenyl, and naphthyl groups.

The term "heteroaryl", as used herein, is understood as being unsaturated rings of five or six atoms containing one or two O- and/or S-atoms and/or one to four N-atoms, provided that the total number of hetero-atoms in the ring is 4 or less. The heteroaryl ring is attached by way of an available carbon or nitrogen atom. Non-limiting examples of heteroaryl groups include 2-, 3-, or 4-pyridyl, 4-imidazolyl, 4-thiazolyl, 2- and 3-thienyl, and 2- and 3-furyl. The term "heteroaryl", as used herein, is understood as also including bicyclic rings wherein the five or six membered ring containing O, S and N-atoms as defined above is fused to a benzene or pyridyl ring. Non-limiting examples of bicyclic rings include but are not limited to 2- and 3-indolyl as well as 4- and 5-quinolinyl.

The term "heteroatom", as used herein, is understood as being oxygen, sulfur or nitrogen.

The term "patient", as used herein, is understood as being any individual treated with the melatonin ligands of the present invention. Patients include humans, as well as other animals such as companion animals and livestock. Patients may be afflicted by a condition associated with MLT activity or may be free of such a condition (i.e. treatment may be prophylactic).

Prodrugs and solvates of the melatonin ligands of the present invention are also contemplated herein. The term "prodrug", as used herein, is understood as being a compound which, upon administration to a subject, undergoes chemical conversion by metabolic or chemical processes to yield a compound of the Formula I, or a salt and/or solvate thereof. Solvates of the compounds of Formula I are preferably hydrates.

The term "derivative" as used herein, is understood as being a substance which comprises the same basic carbon skeleton and carbon functionality in its structure as a given compound, but can also bear one or more substituents or rings.

The term "analogue" as used herein, is understood as being a substance similar in structure to another compound but differing in some slight structural detail.

The term "antagonist" as used herein, is understood as being any molecule that blocks, inhibits, or neutralizes a biological activity of the high affinity MLT receptors subtypes $MT_2$ and/or $MT_1$. In a similar manner, the term "agonist" as used herein, is understood as being any molecule that mimics a biological activity of native MLT. The term "partial agonist" as used herein, is understood as being any molecule that mimics the activity of endogenous MLT but is unable to achieve the maximal activity of MLT. The term "inverse agonist" as used herein, is understood as being any molecule that by itself elicits effects opposite to that of endogenous MLT. The term "partial inverse agonist" as used herein, is understood as being any molecule that by itself elicits effects opposite to that of endogenous MLT but in a lesser extent than an "inverse agonist".

The term "salt(s)" as used herein, is understood as being acidic and/or basic salts formed with inorganic and/or organic acids or bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps.

Examples of acid addition salts include but are not limited to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, phosphoric, 2-hydroxyethanesulfonate, lactate, maleate, mandelate, methanesulfonate, 2-naphthalenesulfonate, nicotinate, oxalate, pectinate, persulfate, 3-phenylpropionate, picrate, pivalate, propionate, succinate, tartrate, thiocyanate, tosylate, and undecanoate.

Examples of base addition salts include but are not limited to alkali metal salts and alkaline earth metal salts. Non limiting examples of alkali metal salts include lithium, sodium and potassium salts. Non-limiting examples of alkaline earth metal salts include magnesium and calcium salts.

It is contemplated that any embodiment discussed in this specification can be implemented with respect to any method or composition of the invention, and vice versa. Furthermore, compositions of the invention can be used to achieve methods of the invention.

The present invention relates to novel melatonin ligands and pharmaceutically acceptable salts thereof having antidepressant activity as well as sleep inducing properties. More specifically, the present invention relates to novel (N,N-disubstituted-aminoalkyl) amido derivatives and pharmaceutically acceptable salts thereof having high binding affinity for the $MT_2$ and/or $MT_1$ melatonin receptors. In an embodiment, the present invention relates to novel melatonin ligands and pharmaceutically acceptable salts thereof comprising Formula I:

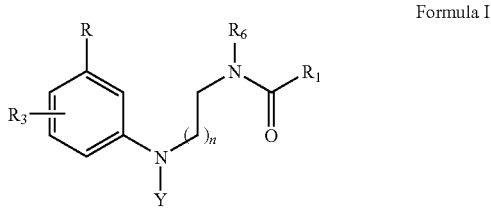

Formula I wherein:
n is 1 or 2;
m is 0, 1 or 2;
p is 0, 1, 2, 3, 4, 5, 6, 7 or 8;
v is 2 or 3;
A is aryl or heteroaryl;
Z is O, S or $NR_8$;
Y is selected from the group consisting of hydrogen, aryl, heteroaryl, $C_1$-$C_6$ alkyl, $C_3$-$C_6$ cycloalkyl, and

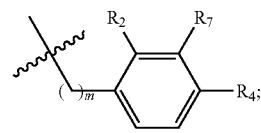

R is selected from the group consisting of hydrogen, hydroxyl, —$OCF_3$, $CF_3$, $C_1$-$C_5$ alkyl, $C_1$-$C_5$ alkyloxy, $C_1$-$C_5$ alkylthio, halogen and —Z—$(CH_2)_p$-A;

$R_1$ is selected from the group consisting of: $C_1$-$C_4$ alkyl, $C_3$-$C_6$ cycloalkyl, $CF_3$, hydroxy-substituted $C_1$-$C_4$ alkyl, hydroxy-substituted $C_3$-$C_6$ cycloalkyl, and $NHR_5$, wherein $R_5$ is $C_1$-$C_3$ alkyl or $C_3$-$C_6$ cycloalkyl;

$R_2$ is selected from the group consisting of: hydrogen, $C_1$-$C_4$ alkyl, $C_1$-$C_4$ alkyloxy, $OCF_3$, $CF_3$, hydroxyl, and halogen;

$R_3$ is selected from the group consisting of hydrogen, $C_1$-$C_4$ alkyl, $C_1$-$C_4$ alkyloxy, $OCF_3$, $CF_3$, hydroxyl, and halogen;

R and $R_3$ may be connected together to form an —O—$(CH_2)_v$ bridge representing with the carbon atoms to which they are attached a 5- or 6-membered heterocyclic ring system;

$R_4$ is selected from the group consisting of hydrogen, $C_1$-$C_4$ alkyl, $C_1$-$C_4$ alkyloxy, $OCF_3$, $CF_3$, hydroxyl, and halogen;

$R_6$ is selected from the group consisting of hydrogen and $C_1$-$C_6$ alkyl;

$R_7$ is selected from the group consisting of hydrogen, $C_1$-$C_4$ alkyl, $C_1$-$C_4$ alkyloxy, $OCF_3$, $CF_3$, hydroxyl, and halogen; and $R_8$ is selected from the group consisting of hydrogen and $C_1$-$C_4$ alkyl.

In an embodiment of the present invention, R is H or methoxy; $R_1$ is methyl, ethyl, propyl, cyclopropyl, cyclobutyl or $NHR_5$, wherein $R_5$ is ethyl.

In an embodiment, the MLT ligands of the present invention are selected from the group consisting of N-[2-(diphenylamino)ethyl]acetamide (5a), N-{2-[(3-Methoxyphenyl)-phenylamino]ethyl}acetamide (5b), N-[2-(bis-3-methoxyphenylamino)ethyl]acetamide (5c), N-{2-[(4-Methoxyphenyl)-3-methoxyphenylamino]ethyl}acetamide (5d), N-{2-[(4-Methoxyphenyl)-phenylamino]ethyl}acetamide (5e), N-{2-[(3-bromophenyl)-phenylamino]ethyl}acetamide (5f), N-{2-[(3-Methoxyphenyl)-β-naphthylamino]ethyl}acetamide (5g), N-{2-[(3-phenylbutoxyphenyl)-phenylamino]ethyl}acetamide (5i), N-{2-[(3-Methoxyphenyl)-methylamino]ethyl}acetamide (5j), N-{2-[(3-Methoxyphenyl)-benzylamino]ethyl}acetamide (5k), N-{2{(3-Methoxyphenyl)-amino]ethyl}acetamide (5l), N-{3-[(3-Methoxyphenyl)-methylamino]propyl}acetamide (5m), N-{2-[(3-Methoxyphenyl)-phenylamino]ethyl}butanamide (5n), N-{2-[(3-Methoxyphenyl)-phenylamino]ethyl}cyclobutancarboxamide (5o), and N-Methyl-N-{2-[(3-methoxyphenyl)-phenylamino]ethyl}acetamide (6).

In an embodiment, some of the MLT ligands of the present invention are partial agonists and show $MT_2$ receptor selectivity.

In yet a further embodiment, the present invention relates to pharmaceutical compositions comprising a therapeutically effective amount of one or more of the melatonin ligands or pharmaceutically acceptable salts thereof as defined herein, and at least one pharmaceutically acceptable excipient, non-limiting examples of which are carriers and diluents. The term "therapeutically effective amount" is understood as being an amount of melatonin ligand or pharmaceutically acceptable salts thereof as defined herein, required upon administration to a patient in order to treat or prohibit a condition associated with MLT activity. Therapeutic methods comprise the step of treating patients in a pharmaceutically acceptable manner with the melatonin ligands or pharmaceutically acceptable salts thereof as disclosed herein, or with compositions comprising such melatonin ligands or pharmaceutically acceptable salts thereof. Such compositions may be in the form of tablets, coated tablets, capsules, caplets, powders, granules, lozenges, suppositories, reconstitutable powders, syrups, liquid preparations such as oral or sterile parenteral solutions or suspensions, as well as injectable formulations and transdermal formulations.

The melatonin ligands or pharmaceutically acceptable salts thereof of the present invention may be administered alone or in combination with pharmaceutically acceptable carriers. The proportion of each carrier is determined by the solubility and chemical nature of the compound, the route of administration, and standard pharmaceutical practice. In order to ensure consistency of administration, in an embodiment of the present invention, the pharmaceutical composition is in the form of a unit dose. The unit dose presentation forms for oral administration may be tablets, coated tablets and capsules and may contain conventional excipients. Non-limiting examples of conventional excipients include binding agents such as acacia, gelatin, sorbitol, or polyvinylpyrrolidone; fillers such as lactose, dextrose, saccharose, sugar, maize-starch, calcium phosphate, sorbitol or glycine; tabletting lubricants such as talc, stearic acid, calcium or magnesium stearate, polyethylene glycols, gums, gels; disintegrants such as starch, polyvinylpyrrolidone, sodium starch glycollate or microcrystalline cellulose; or pharmaceutically acceptable wetting agents such as sodium lauryl sulphate.

The melatonin ligands or pharmaceutically acceptable salts thereof of the present invention may be injected parenterally; this being intramuscularly, intravenously, or subcutaneously. For parenteral administration, the melatonin ligands or pharmaceutically acceptable salts thereof may be used in the form of sterile solutions containing solutes for example, sufficient saline or glucose to make the solution isotonic.

The melatonin ligands or pharmaceutically acceptable salts thereof of the present invention may also be administered via transdermal routes using dermal or skin patches.

The melatonin ligands or pharmaceutically acceptable salts thereof may be administered orally in the form of tablets, coated tablets, capsules, or granules, containing suitable excipients non-limiting examples of which are starch, lactose, white sugar and the like. The melatonin ligands or pharmaceutically acceptable salts thereof may be administered orally in the form of solutions which may contain coloring and/or flavoring agents. The melatonin ligands or pharmaceutically acceptable salts thereof may also be administered sublingually in the form of tracheas or lozenges in which the active ingredient(s) is/are mixed with sugar or corn syrups, flavoring agents and dyes, and then dehydrated sufficiently to make the mixture suitable for pressing into solid form.

The solid oral compositions may be prepared by conventional methods of blending, granulation, compression, coating, filling, tabletting, or the like. Repeated blending operations may be used to distribute the active agent throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, suspensions, syrups, or elixirs, or may be presented as a dry product for reconstitution with water or other suitable vehicle before use. Such liquid preparations may or may not contain conventional additives. Non limiting examples of conventional additives include suspending agents such as sorbitol, syrup, natural gums, agar, methyl cellulose, gelatin, pectin, sodium alginate, hydroxyethylcellulose, carboxymethylcellulose, aluminum stearate gel, or hydrogenated edible fats; emulsifying agents such as sorbitan monooleate or acaci; non-aqueous vehicles (which may include edible oils) such as almond oil, fractionated coconut oil, oily esters selected from the group consisting of glycerine, propylene glycol, ethylene glycol, and ethyl alcohol; preservatives such as for instance methyl para-hydroxybenzoate, ethyl para-hydroxybenzoate, n-propyl parahydroxybenzoate, n-butyl parahydroxybenzoate or sorbic acid; and, if desired conventional flavoring such as saccharose, glycerol, mannitol, sorbitol, or coloring agents.

For parenteral administration, fluid unit dosage forms may be prepared by utilizing the melatonin ligands or pharmaceutically acceptable salts thereof and a sterile vehicle (i.e. sterile water), and, depending on the concentration employed, the melatonin ligands or pharmaceutically acceptable salts thereof may be either suspended or dissolved in the vehicle. Other suitable vehicles may include olive oil, ethyl oleate, and glycols. If needed, a suitable quantity of lidocaine hydrochloride may also be included. Once in solution, the melatonin ligands or pharmaceutically acceptable salts thereof may be injected and filter sterilized before filling a suitable vial or ampoule followed by subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying). Parenteral suspensions may be prepared in substantially the same manner, except that the melatonin ligands or pharmaceutically acceptable salts thereof should be suspended in the vehicle rather than being dissolved, and, further, sterilization is not achievable by filtration. The melatonin ligands or pharmaceutically acceptable salts thereof may be sterilized, however, by exposing it to ethylene oxide before suspending it in the sterile vehicle. A surfactant or wetting solution may be advantageously included in the composition to facilitate uniform distribution of the melatonin ligands or pharmaceutically acceptable salts thereof.

The melatonin ligands or pharmaceutically acceptable salts thereof may be administered in the form of suppositories. Suppositories may contain pharmaceutically acceptable vehicles such as cocoa butter, polyethylene glycol, sorbitan, esters of fatty acids, lecithin and the like.

The pharmaceutical compositions of the present invention comprise a pharmaceutically effective amount of at least one melatonin ligand or pharmaceutically acceptable salt thereof as described herein and one or more pharmaceutically acceptable carriers, excipients or diluents. In an embodiment of the present invention, the pharmaceutical compositions contain from about 0.1% to about 99% by weight of a melatonin ligand or pharmaceutically acceptable salt thereof as disclosed herein. In a further embodiment of the present invention, the pharmaceutical compositions contain from about 10% to about 60% by weight of a melatonin ligand or pharmaceutically acceptable salt thereof as disclosed herein, depending on which method of administration is employed. Physicians will determine the most-suitable dosage of the present therapeutic agents (the melatonin ligands or pharmaceutically acceptable salts thereof). Dosages may vary with the mode of administration and the particular melatonin ligand chosen. In addition, the dosage may vary with the particular patient under treatment. The dosage of the melatonin ligand or pharmaceutically acceptable salt thereof used in the treatment may vary, depending on the degree of MLT activity, the relative efficacy of the compound and the judgment of the treating physician.

In a non-limiting embodiment, the MLT ligands of the present invention are suitable for oral administration.

In an embodiment of the present invention, the pharmaceutical compositions comprise a therapeutically effective amount of one or more of the melatonin ligands or pharmaceutically acceptable salts thereof as defined herein, and at least one pharmaceutically acceptable excipient, non-limiting examples of which are carriers and diluents.

Materials and Methods

Melting points were determined using a Buchi B-540 capillary melting point apparatus and are uncorrected. $^1$H NMR spectra were recorded using a Bruker AVANCE 200 MHz spectrometer, using $CDCl_3$ as the reference solvent unless specified otherwise. Chemical shifts (δ scale) are reported in parts per million (ppm) relative to the central peak of the reference solvent. EI-MS spectra (70 eV) were taken using a Fisons Trio 1000 instrument. Molecular ions ($M^+$) and base peaks only are provided herein. Infrared spectra were obtained using a Nicolet Avatar 360 FT-IR spectrometer; absorbancies are reported in ν ($cm^{-1}$). Elemental analyses for C, H and N were performed using a Carlo Erba analyzer. Column chromatography purifications were performed under "flash" conditions using Merck 230-400 mesh silica gel. Analytical thin-layer chromatography (TLC) was carried out on Merck silica gel 60 $F_{254}$ plates. All chemicals were purchased from commercial suppliers and used directly without any further purification.

In an embodiment, the compounds of Formula (I) may be prepared by procedures such as those illustrated in general Scheme 1. Other procedures, as well as variations thereof, could also be employed for preparing the compounds of Formula (I) and would be within the ability of one of ordinary skill in the art.

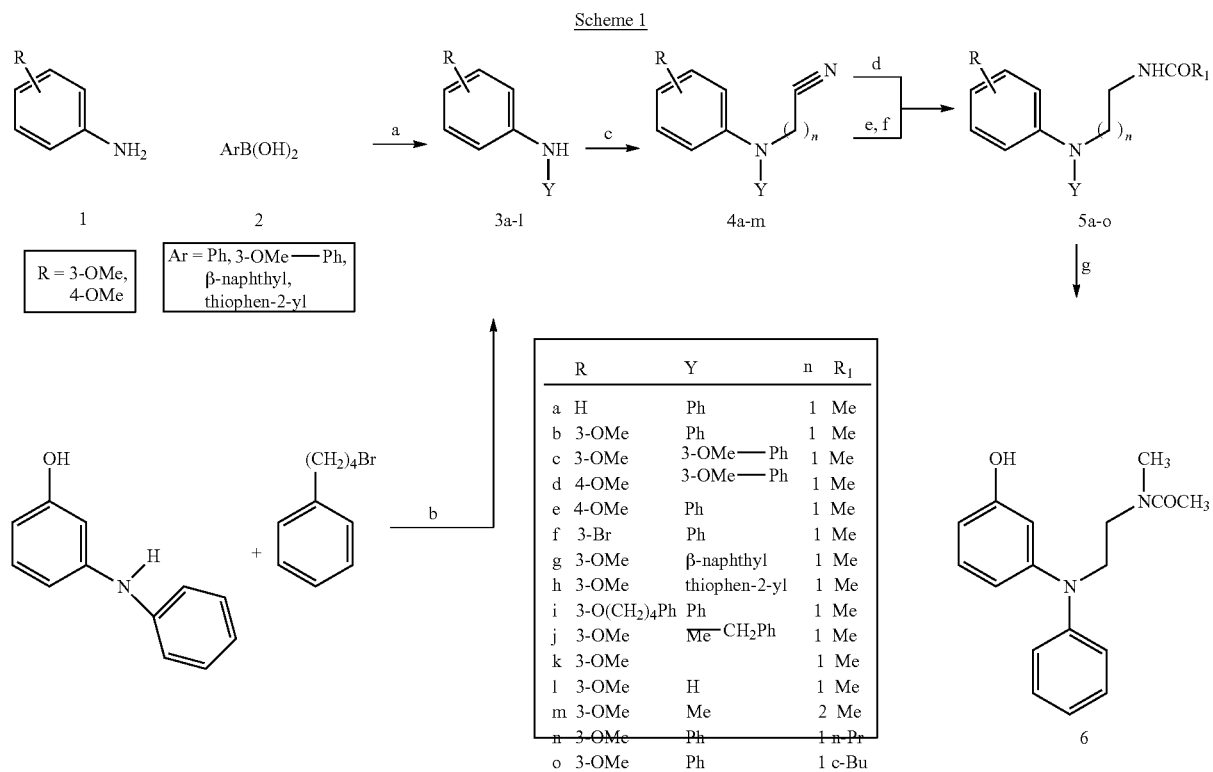

Reagents: (a) Cu(OAc)$_2$, CH$_2$Cl$_2$, pyridine, room temperature; (b) KOH, EtOH, reflux; (c) BrCH$_2$CN or BrCH$_2$CH$_2$CN, DMF, NaH, 100° C.; (d) H$_2$, Ni/Raney, 4 atm, (R$_1$CO)$_2$O, THF or H$_2$, Ni/Raney, NH$_3$/EtOH, 4 atm, then c-Butanoyl chloride/TEA for 5o; (e) LiAlH$_4$, THF for 5k; (f) Ac$_2$O, TEA, THF; (g) MeI, NaH, DMF.

The (aminoalkyl)-amido derivatives (5a-o) were prepared by N-cyanoalkylation of the corresponding secondary amines (3a-k) with bromoacetonitrile or bromoproprionitrile in the presence of sodium hydride, followed by reduction of the intermediate nitriles (4a-m) and N-acylation of the crude N,N-disubstituted diamines with anhydrides, acid chloride or isocyanates (Scheme 1).

The key N,N-diarylamines (3c-e and 3g,h) were obtained by the coupling reaction between an arylboronic acid (2) and an appropriate aniline (1) in the presence of cupric acetate and pyridine, according to a previously reported procedure [Chan, D. M. T.; Monaco, K. L. *Tetrahedron Letters* 1998, 39, 2933-2936]. Alternatively, the N,N-diarylamines (3c-e and 3g,h) can be obtained by condensation of a suitable acetanilide with 3-bromoanisole (Akhavan-Tafti et al. *Tetrahedron Letters* 1988, 63, 930]. The N,N-diphenylamines (3a-b,f) and N-methyl-3-methoxyaniline (3j) were commercially available. The N,N-diarylamine 31 was obtained by the alkylation of 3-hydroxy-diphenylamine using 1-bromo-4-phenylbutane. N-benzyl-3-methoxyaniline (3k) was prepared as previously described [Tietcheu, C.; Garcia, C. et al. *J. Heterocyclic Chem.* 2002, 39, 965-973]. The cyano group of nitriles 4a-m was easily reduced using standard procedures well known to those of skilled in the art. Briefly, Raney nickel hydrogenation of nitriles 4a-j and 4l-m followed by in situ N-acylation with the suitable anhydride provided the desired melatonin ligands 5a-j and 5l-n. The cycloalkanecarboxamido derivatives [$R_1$=$C_3$-$C_6$ cycloalkyl, i.e. 5o] were prepared by hydrogenation of the corresponding nitrile over Raney nickel in the presence of $NH_3$-EtOH, followed by N-acylation with a carbocyclic acyl chloride in the presence of triethylamine (TEA). To prepare the N-benzyl derivative 5k the corresponding nitrile was reduced with lithium aluminum hydride, and the resulting crude amine N-acylated with a suitable anhydride. Compound 6 was prepared by N-alkylation of 5b with MeI in the presence of NaH.

It is important to note that depending on the type of substituent on the phenyl ring (i.e. "R"), it is possible to further transform the compounds of Formula (I) into analogues thereof using procedures within the ability of one of ordinary skill in the art. For example, in order to prepare compounds of Formula (I) in which R is $C_1$-$C_8$ alkylthio, $C_2$-$C_8$ alkyloxy or phenylalkyloxy, the corresponding compound of Formula (I) in which R is OMe can be reacted with $AlCl_3$ or $BBr_3$ and the desired alkyl halide according to previously reported literature procedures [Caubere C., Cauber P., Renard P. et al. *Tetrahedron* 1994, 50, 13433-48]. Non-limiting examples of compounds prepared according to this procedure include N-{2-[(3-Butoxyphenyl)-methylamino]ethyl}acetamide: mp=68° C.; EI-MS 264 ($M^+$), 192 (100); N-{2-[(3-Hexyloxyphenyl)-methylamino]ethyl}acetamide: mp=56° C.; EI-MS 292 ($M^+$), 220 (100); and N-{2-{[3-(4-phenylbutoxy)phenyl)-methylamino]}ethyl}acetamide: mp=57° C.; EI-MS 340 ($M^+$), 268 (100).

Results

N-[2-(diphenylamino)ethyl]acetamide (5a)

A solution of N,N-diphenylamine (3a) (2 mmol) in dry DMF (5 mL) was added dropwise to a stirred suspension of sodium hydride (150 mg of an 80% dispersion in mineral oil) in dry DMF (5 mL) at 0° C. under a $N_2$ atmosphere. The mixture was stirred at 0° C. for 30 minutes. Bromoacetonitrile (0.65 mL) was subsequently added and the resulting mixture was heated at 100° C. for 24 h. The reaction mixture was poured into ice/water (80 g), and then extracted 3× with ethyl acetate. The organic phases were combined, washed with brine, dried ($Na_2SO_4$) and concentrated under reduced pressure to provide a crude residue which was purified by flash chromatography (silica gel; cyclohexane/EtOAc 9:1 as eluent). Yield (4a): 36%; mp 44-45° C. (ether/petroleum ether).

A solution of the nitrile (4a) (1 mmol) in THF (10 mL) and acetic anhydride (3 mL) was hydrogenated over Raney nickel at 4 atm of $H_2$ for 5 h at 60° C. The catalyst was filtered over Celite, the filtrate was concentrated in vacuo, and the residue was partitioned between ethyl acetate and 2N NaOH. The organic layer was washed with brine, dried ($Na_2SO_4$) and evaporated under reduced pressure. Purification by flash chromatography (silica gel; EtOAc as eluent) followed by crystallization gave the desired melatonin ligand (5a). Yield 78%; mp 102-103° C. (ether/petroleum ether). EI-MS 254 ($M^+$), 182 (100). $^1$H-NMR ($CDCl_3$): δ 1.93 (s, 3H), 3.50 (m, 2H), 3.90 (t, 2H), 5.77 (brs, 1H), 6.95-7.07 (m, 6H), 7.25-7.33 (m, 4H).

N-{2-[(3-Methoxyphenyl)-phenylamino] ethyl}acetamide (5b)

The title compound was obtained by hydrogenation of the corresponding nitrile (4b) [mp 53-54° C. (petroleum ether); EI-MS 238 ($M^+$, 100)], prepared (yield: 38%) following the procedure as described hereinabove, and starting from N-(3-Methoxyphenyl)-aniline (3b). Yield: 85%; mp 73-74° C. (isopropyl ether). EI-MS 284 ($M^+$), 212 (100). $^1$H-NMR ($CDCl_3$): δ 1.93 (s, 3H), 3.50 (m, 2H), 3.76 (s, 3H), 3.89 (t, 2H), 5.77 (brs, 1H), 6.50-6.63 (m, 3H), 6.99-7.35 (m, 6H).

N-[2-(bis-3-methoxyphenylamino)ethyl]acetamide (5c)

Cupric acetate (2.1 mmol) and pyridine (0.25 ml) were added to a vigorously stirred solution of 3-methoxyaniline (1 mmol) and 3-methoxyphenylboronic acid (2 mmol) in dry methylene chloride (3.5 ml), under a nitrogen atmosphere. The reaction mixture was stirred at room temperature for 72 h (the progress of the reaction was monitored by TLC). N-(3-Methoxyphenyl)-3-methoxyaniline (3c) was isolated by direct flash chromatography of the crude reaction mixture following preabsorption on silica gel. Yield (3c): 25%; EI-MS 229 ($M^+$) [Lit.: Urgaonkar, S.; Verkade, J. G. *J. Org. Chem.* 2004, 69, 9135-9142].

N-cyanomethylation of 3c with bromoacetonitrile, according to the method previously described for the preparation of 4a, provided 2-[(bis-3-methoxyphenyl)amino)]acetonitrile (4c). Yield (4c): 37% (oil); EI-MS 268 ($M^+$, 100). Compound (4c) was then hydrogenated according to the procedure previously described for the preparation of 5a to provide the title compound 5c. Yield (5c): 53%; mp 84-85° C. (ether/petroleum ether); EI-MS 314 ($M^+$), 242 (100). $^1$H-NMR ($CDCl_3$): δ1.94 (s, 3H), 3.50 (m, 2H), 3.77 (s, 6H), 3.87 (t, 2H), 5.63 (brs, 1H), 6.51-6.68 (m, 6H), 7.19 (m, 2H).

N-{2-[(4-Methoxyphenyl)-3-methoxyphenylamino] ethyl}acetamide (5d)

The title compound was prepared according to the method previously described for the preparation of 5c, by hydrogenation of the nitrile 4d [Yield (4d): 58%; EI-MS 268 ($M^+$), 131 (100); $^1$H-NMR ($CDCl_3$): δ 3.75 (s, 3H), 3.84 (s, 3H), 4.46 (s, 2H), 6.31-652 (m, 3H), 6.92-6.97 (m, 2H), 7.15-7.23 (m, 3H)], prepared by N-cyanomethylation of 3d [Yield (3d): 32%; EI-MS 229 ($M^+$); $^1$H-NMR ($CDCl_3$): δ 3.77 (s, 3H), 3.81 (s, 3H), 6.45 (m, 3H), 6.88 (m, 2H), 7.12 (m, 3H)]. Yield (5d): 84%; $^1$H-NMR ($CDCl_3$): δ1.94 (s, 3H), 3.48 (m, 2H), 3.74 (s, 3H), 3.76 (m, 2H), 3.82 (s, 3H), 5.67 (brs, 1H), 6.33-6.41 (m, 3H), 6.90 (m, 2H), 7.05-7.14 (m, 3H).

N-{-2-[(4-Methoxyphenyl)-phenylamino] ethyl}acetamide (5e)

The title compound was prepared according to the method previously described for the preparation of 5c, by hydrogenation of the nitrile 2-[(4-methoxyphenyl)-phenylamino]acetonitrile (4e) [Yield (4e): 38%; mp 102-104° C. (ether/petroleum ether); EI-MS 238 ($M^+$, 100)], prepared by N-cyanomethylation of 3e [Elhalem, E.; Bailey, B. N.;

Docampo, R. *J. Med. Chem.* 2002, 45, 3984-3999]. Yield (5e): 30%; mp 85-86° C. (ether/petroleum ether); EI-MS 284 (M$^+$), 212 (100); $^1$H-NMR (CDCl$_3$): δ 1.94 (s, 3H), 3.49 (m, 2H), 3.80 (m, 2H), 3.82 (s, 3H), 5.70 (brs, 1H), 6.75-6.93 (m, 5H), 7.07-7.20 (m, 4H).

N-{2-[(3-bromophenyl)-phenylamino]ethyl}acetamide (5f)

A solution of nitrile 4f (1.16 mmol), prepared according to the method previously described for the preparation of 4a, but starting with N-(3-bromophenyl)-aniline (3f) [yield (4f): 37%; oil; $^1$H-NMR (CDCl$_3$): δ 4.50 (s, 2H), 6.87 (m, 1H), 7.08-7.46 (m, 8H)] in dry THF (6 mL), was hydrogenated according to the procedure previously described for the preparation of 5a to provide the title compound 5f. The crude product was purified by flash-chromatography on silica gel (dichloromethane/acetone, 95:5 as eluent). Yield (5f): 20%; $^1$H-NMR (CDCl$_3$): δ 1.90 (s, 3H), 3.48 (m, 2H), 3.85 (m, 2H), 6.03 (brs, 1H), 6.81-7.41 (m, 9H).

N-{2-[(3-Methoxyphenyl)-β-naphthylamino]ethyl}acetamide (5g)

The title compound was prepared according to the method previously described for the preparation of 5c, followed by hydrogenation of the nitrile 2-[(3-methoxyphenyl)-3-naphthylamino]acetonitrile (4g) [Yield (4g): 28%; oil; EI-MS 288 (M$^+$, 100); $^1$H-NMR (CDCl$_3$): δ 3.77 (s, 3H), 4.64 (s, 2H), 6.62-6.72 (m, 3H), 7.18-7.81 (m, 8H)], prepared by N-cyanomethylation of N-(3-methoxyphenyl)-β-naphthylamine 3g [Yield (3g): 23%; EI-MS 249 (M$^+$, 100); $^1$H-NMR (CDCl$_3$): δ 3.81 (s, 3H), 5.91 (brs, 1H), 6.53-7.53 (m, 11H)]. Yield (5g): 48%; oil; EI-MS 334 (M$^+$), 262 (100); $^1$H-NMR (CDCl$_3$): δ 1.92 (s, 3H), 3.54 (m, 2H), 3.76 (s, 3H), 3.99 (t, 2H), 5.89 (brt, 1H), 6.52-6.69 (m, 3H), 7.15-7.74 (m, 8H).

N-{2-[(3-phenylbutoxyphenyl)-phenylamino]ethyl}acetamide (5i)

A mixture of N-(3-hydroxyphenyl)aniline (2.7 mmol) and 1-bromo-4-phenylbutane (2.02 mmol) was refluxed for 5 h in a 10% ethanol solution of KOH. The reaction mixture was cooled to room temperature, poured into water and extracted three times with EtOAc. The combined organic phases were washed with brine, dried (Na$_2$SO$_4$) and evaporated under reduced pressure to provide a residue which was purified by flash chromatography (silica gel; cyclohexane/EtOAc, 8:2 as eluent). Yield N-(3-phenylbutoxyphenyl)-aniline (3i): 86%; oil; EI-MS 317 (M$^+$), 91 (100); $^1$H-NMR (CDCl$_3$): δ1.83 (m, 4H), 2.68 (m, 2H), 3.96 (m, 2H), 5.75 (br, 1H), 6.46-7.38 (m, 14H).

N-cyanomethylation of amine 3i, followed by hydrogenation and N-acetylation of the intermediate nitrile 4i [Yield (4i): 38%; oil; EI-MS 356 (M$^+$), 91 (100); $^1$H-NMR (CDCl$_3$): δ 1.80 (m, 4H), 2.67 (m, 2H), 3.93 (m, 2H), 4.51 (s, 2H), 6.53-6.65 (m, 3H), 7.06-7.40 (m, 11H)], according to the procedure previously described for the preparation of 5c, provided the title compound 5i. Yield (5i): 30%; EI-MS 402 (M$^+$), 330 (100); $^1$H-NMR (CDCl$_3$): δ 1.80 (m, 4H), 1.92 (s, 3H), 2.68 (m, 2H), 3.50 (m, 2H), 3.90 (m, 4H), 5.61 (brs, 1H), 6.46-6.61 (m, 3H), 6.95-7-38 (m, 11H).

N-{2-[(3-Methoxyphenyl)-methylamino]ethyl}acetamide (5j)

N-cyanomethylation of N-methyl-3-methoxyaniline (3j), followed by hydrogenation and N-acetylation of the intermediate nitrile 4j [Yield (4j): 88%; oil; $^1$H-NMR (CDCl$_3$): δ 3.00 (s, 3H), 3.82 (s, 3H), 4.15 (s, 2H), 6.40-6.52 (m, 3H), 7.24 (m, 1H)], according to the procedure previously described for the preparation of 5a, provided the title compound 5j. Yield (5j): 49%; mp 69-71° C. (ether/petroleum ether); EI-MS 222 (M$^+$), 150 (100); $^1$H-NMR (CDCl$_3$): δ 1.97 (s, 3H), 3.01 (s, 3H), 3.45 (m, 4H), 3.81 (s, 3H), 5.73 (brs, 1H), 6.30-6.50 (m, 3H), 7.17 (m, 1H).

N-{2-[(3-Methoxyphenyl)-benzylamino]ethyl}acetamide (5k)

A solution of nitrile 4k (1.16 mmol), prepared according to the method previously described for the preparation of 4a, but starting with N-benzyl-3-methoxyaniline (3k) [Tietcheu, C.; Garcia, C. *J. Heterocyclic Chem.* 2002, 39, 965-973] [yield (4k): 70%; EI-MS 252 (M$^+$), 91 (100); $^1$H-NMR (CDCl$_3$): δ 3.80 (s, 3H), 4.10 (s, 2H), 4.53 (s, 2H), 6.50-6.61 (m, 3H), 7.20-7.41 (m, 6H)], was added dropwise to a stirred, ice-cooled suspension of LiAlH$_4$ (0.088 g, 2.3 mmol) in dry THF (11 mL) under nitrogen, and the resulting mixture was stirred at room temperature for 3.5 h. The reaction mixture was cooled to 0° C. and the excess hydride was cautiously destroyed using water. The resulting mixture was filtered over a Celite pad, the filtrate concentrated in vacuo and partitioned between EtOAc and 2N NaOH (pH=10). The combined organic phases were washed once with brine, dried (Na$_2$SO$_4$) and evaporated to afford a crude oily amine which was then used without any further purification.

TEA (1.1 equiv.) and acetic anhydride (1.1 equiv.) were added to a cold solution of the above crude amine (1 mmol) in THF (4 mL) and the resulting reaction mixture was left stirring at room temperature for 2 h. The solvent was subsequently evaporated under reduced pressure and the crude residue, was taken up in ethyl acetate and washed with a saturated aqueous solution of NaHCO$_3$ followed by washing with brine. After drying over Na$_2$SO$_4$, the solvent was distilled off in vacuo and the residue was purified by flash-chromatography (silica gel; cyclohexane/EtOAc, 9:1 as eluent). Yield (5k): 20%; oil; EI-MS 298 (M$^+$), 91 (100); $^1$H-NMR (CDCl$_3$): δ 1.86 (s, 3H), 3.52 (m, 4H), 3.78 (s, 3H), 4.57 (s, 2H), 5.63 (br, 1H), 6.35 (m, 3H), 7.11-7.38 (m, 6H).

N-[2{(3-Methoxyphenyl)-amino]ethyl}acetamide (5l)

N-cyanoalkylation of 3-methoxyaniline (3l) using chloroacetonitrile, followed by hydrogenation and N-acetylation of the intermediate nitrile 4l [Yield (4l): 58%; $^1$H-NMR (CDCl$_3$): δ 3.80 (s, 3H), 4.05 (s, 2H), 6.25-6.48 (m, 2H), 7.18 (t, 1H)], according to the procedure previously described for the preparation of 5a, provided the title compound 5l; oil. $^1$H-NMR (CDCl$_3$): δ 2.00 (s, 3H), 3.27 (m, 2H), 3.53 (m, 2H9, 3.78 (s, 3H), 5.84 (brs, 1H), 6.17-6.32 (m, 3H), 7.09 (t, 1H).

N-{3-[(3-Methoxyphenyl)-methylamino]propyl}acetamide (5m)

N-cyanoalkylation of N-methyl-3-methoxyaniline (3j) with 3-bromopropionitrile, followed by hydrogenation and N-acetylation of the intermediate propionitrile 4m [Yield (4m): 88%; oil; $^1$H-NMR (CDCl3): δ 2.57 (t, 2H), 3.02 (s, 3H), 3.70 (t, 2H), 3.80 (s, 3H), 6.25 (t, 1H), 6.31-6.38 (m, 2H), 7.18 (t, 1H)], according to the procedure previously described for the preparation of 5a, provided the title compound 5m. Yield (5m): 52%; oil. $^1$H-NMR (CDCl3): δ 1.80 (m, 2H), 1.95

(s, 3H), 2.91 (s, 3H), 3.24-3.40 (m, 4H), 3.80 (s, 3H), 5.60 (brs, 1H), 6.24-6.37 (m, 3H), 7.15 (t, 1H).

N-{2-[(3-Methoxyphenyl)-phenylamino]ethyl}butanamide (5n)

The title compound was prepared according to the method previously described for the preparation of 5b, by hydrogenation of nitrile (4b) followed by N-acylation with butyric anhydride. Yield (5n): 80%; mp 50-52° C. (petroleum ether); $^1$H-NMR (CDCl$_3$): δ 0.92 (t, 3H), 1.59 (m, 2H), 2.10 (t, 2H), 3.52 (m, 2H), 3.76 (s, 3H), 3.89 (t, 2H), 5.71 (brs, 1H), 6.55-6.61 (m, 3H), 7.02-7.31 (m, 6H).

N-{2-[(3-Methoxyphenyl)-phenylamino]ethyl}cyclobutancarboxamide (5o)

A solution of nitrile 4b (1.6 mmol) in THF (7 mL) and 2N NH$_3$ in EtOH (5 mL) was hydrogenated over Raney nickel at 4 atm of H$_2$ for 6 h at 60° C. The catalyst was filtered over a Celite pad, the filtrate concentrated in vacuo, and the residue partitioned between EtOAc and water. The organic phase was washed with brine, dried (Na$_2$SO$_4$) and evaporated under reduced pressure to give a crude oily amine which was used without any further purification.

TEA (1.1 equiv.) and cyclobutanecarbonyl chloride (1.1 equiv.) were added to a cold solution of the above crude amine (1 mmol) in THF (4 mL) and the resulting reaction mixture was left stirring at room temperature for 2 h. The solvent was subsequently evaporated under reduced pressure and the residue was taken up in ethyl acetate and washed with a saturated aqueous solution of NaHCO$_3$ followed by washing with brine. After drying over Na$_2$SO$_4$, the solvent was distilled off in vacuo to give a crude product, which was subsequently purified by flash-chromatography on silica gel (cyclohexane/EtOAc, 9:1 as eluent). Yield (5o): 56%; mp 64-65° C. (ether/petroleum ether); $^1$H-NMR (CDCl$_3$): δ 1.82-2.26 (m, 6H), 2.90 (m, 1H), 3.52 (m, 2H), 3.76 (s, 3H), 3.90 (t, 2H), 5.63 (brs, 1H), 6.50-6.67 (m, 3H), 7.03-7.35 (m, 6H).

N-methyl-N-{2-[3-Methoxyphenyl)-phenylamino]ethyl}acetamide (6)

A solution of 5b (1 mmol) in dry DMF (2.5 mL) was added dropwise to a stirred suspension of sodium hydride (75 mg of an 80% dispersion in mineral oil) in dry DMF (2.5 mL) at 0° C. under N$_2$ atmosphere. The mixture was stirred at 0° C. for 40 min. Iodomethane (1.2 mmol) was then added and the resulting mixture was stirred at room temperature for 16 h. The reaction mixture was poured into ice/water (40 g), and extracted 3× with ethyl acetate. The organic phases were combined, washed with brine, dried (Na$_2$SO$_4$) and concentrated under reduced pressure to give a crude residue which was purified by flash chromatography (silica gel, cyclohexane/EtOAc 9:1 as eluent). Yield (6): 72%; oil; EI-MS 298 (M$^+$), 212 (100); $^1$H-NMR (CDCl$_3$): δ 2.07 (s, 3H), 2.97 (s, 3H), 3.61 (m, 2H), 3.77 (s, 3H), 3.91 (m, 2H), 6.42-6.72 (m, 3H), 6.95-7.34 (m, 6H).

Measurement of Melatonin Binding

The melatonin binding affinities of the compounds of Formula (I) were determined using 2-[$^{125}$I]iodomelatonin as the labeled ligand in competition experiments on cloned human MT$_1$ and MT$_2$ receptors expressed in NIH3T3 rat fibroblast cells. The characterization of NIH3T3-MT$_1$ and NIH3T3-MT$_2$ cells has been previously described [i) Normo, R.; Lucini, V.; Pannacci, M.; Mazzucchelli, C.; Angeloni, D.; Fraschini, F.; Stankov, B. M. Br. J. Pharmacol. 1998, 124, 485-492; ii) Normo, R.; Pannacci, M.; Lucini, V.; Angeloni, D.; Fraschini, F.; Stankov, B. M. Br. J. Pharmacol. 1999, 127, 1288-1294]. Membranes were incubated for 90 min at 37° C. in binding buffer (Tris/HCl 50 mM, pH 7.4). The final membrane concentration was 5-10 μg of protein per tube. The membrane protein level was determined in accordance with previously reported methods [Bradford, M. M. Anal. Biochem. 1976, 72, 248-254]. 2-[$^{125}$I]Iodomelatonin (100 pM) and different concentrations of the compounds of Formula (I) were incubated with the receptor preparation for 90 min at 37° C. Nonspecific binding was assessed with 10 μM MLT; IC$_{50}$ values were determined by nonlinear fitting strategies using the program PRISM (GraphPad SoftWare Inc., San Diego, Calif.). The pK$_i$ values were calculated from the IC$_{50}$ values in accordance with the Cheng-Prusoff equation [Cheng, Y. C.; Prusoff, W. H. Biochem. Pharmacol. 1973, 22, 3099-3108]. The pK$_i$ values are the mean of at least three independent determinations performed in duplicate. To define the functional activity of the compounds of Formula (I) at the MT$_1$ and MT$_2$ receptor subtypes, [$^{35}$S]GTPγS binding assays in NIH3T3 cells expressing human-cloned MT$_1$ or MT$_2$ receptors were performed. The amount of bound [$^{35}$S]GTPγS is proportional to the level of analogue-induced G-protein activation and is related to the intrinsic activity of the compound (i.e. a compound of Formula (I)) under study. The detailed description and validation of this method have been previously reported [Spadoni, G.; Balsamini, C.; Bedini, A.; Diamantini, G.; Di Giacomo, B.; Tontini, A.; Tarzia, G.; Mor, M.; Plazzi, P. V.; Rivara, S.; Normo, R.; Panacci, M.; Lucini, V.; Fraschini, F.; Stankov, B. M. J. Med. Chem. 1998, 41, 3624-3634]. Membranes (15-25 μg of protein, final incubation volume 100 μL) were incubated at 30° C. for 30 min in the presence and in the absence of the MLT analogues, in an assay buffer consisting of [$^{35}$S]GTPγS (0.3-0.5 nM), GDP (50 μM), NaCl (100 mM), and MgCl$_2$ (3 mM). Nonspecific binding was assessed using non-radiolabeled GTPγS (10 μM). In cell lines expressing human MT$_1$ or MT$_2$ receptors, MLT produced a concentration dependent stimulation of basal [$^{35}$S] GTPγS binding, with a maximal stimulation above basal levels of 370% and 250% in MT$_1$ and MT$_2$ respectively. Basal stimulation is the amount of [$^{35}$S]GTPγS specifically bound in the absence of the compounds of Formula (I) and was taken as 100%. The maximal G-protein activation was measured in each experiment by using MLT (100 nM). The compounds of Formula (I) were added at three different concentrations (one concentration being equivalent to 100 nM MLT, a second one 10 times smaller, and a third one 10 times larger), and the percent stimulation above basal was determined. The equivalent concentration was estimated on the basis of the ratio of the affinity of the test compound (compounds of Formula (I)) over that of MLT. It was assumed that at the equivalent concentration the test compound occupies the same number of receptors as 100 nM MLT. All of the measurements were performed in triplicate. The relative intrinsic activity (IA$_r$) values were obtained by dividing the maximum ligand-induced stimulation of [$^{35}$S]GTPγS binding by that of MLT as measured in the same experiment.

Most compounds of the present invention (compounds of Formula (I)) have good to high affinity for MT$_1$ and/or MT$_2$ melatonin receptors, as determined in receptor binding assays, and show better affinity for the MT$_2$ than for the MT$_1$ receptor. For example, the novel compound 5b exhibits better MT$_2$ affinity (pK$_i$=10.18) than melatonin (pK$_i$=9.62) and has about a 100-fold higher affinity for the MT$_2$ (pK$_i$=10.18) than for the MT$_1$ (pK$_i$=8.38) subtype at human recombinant receptors expressed in NIH3T3 cells. Furthermore, compound 5b produced a concentration dependent maximal stimulation of basal [$^{35}$S]GTPγS binding lower than that produced by melatonin, which is indicative that 5b behaves as a partial agonist [the relative intrinsic activity values of 5b (obtained by dividing the maximum 5b-induced G-protein activation by that of MLT) are the following: $IA_r$–$hMT_1$=0.8; $IA_r$–$hMT_2$=0.6] (Table 1).

the water bath for 15 minutes (pre-test). During this time, the rats usually struggle to escape, but eventually adopt a posture of immobility in which they emit only the minimal movements necessary to keep their heads above water. The actual test (5 min) occurs 24 h later. When re-immersed in the water, immobility is increased; antidepressant treatments reliably reduce immobility during the test. The FST is both sensitive and selective for clinically effective antidepressants, has been

TABLE 1

Binding Affinity and Intrinsic Activity ($IA_r$) of some (N,N-disubstituted-aminoalkyl)-amides (Formula II) for the Human $MT_1$ and $MT_2$ Melatonin Receptors Stably Expressed in NIH3T3 Cells.

Formula II

|  |  |  |  |  | $MT_1$ | | | $MT_2$ | | |
|---|---|---|---|---|---|---|---|---|---|---|
| R | Y | n | $R_1$ | $R_6$ | $pK_i^a$ | $IA_r \pm SEM^b$ | Activity$^c$ | $pK_i^a$ | $IA_r \pm SEM^b$ | Activity$^c$ |
| MLT |  |  |  |  | 9.85 ± 0.09 | 1.0 ± 0.01 | A | 9.62 ± 0.10 | 1.01 ± 0.01 | A |
| 5a | H | Ph | 1 | Me | H | 6.90 ± 0.04 | 0.10 ± 0.03 | ANT | 8.41 ± 0.13 | 0.57 ± 0.04 | PA |
| 5b | 3-OMe | Ph | 1 | Me | H | 8.38 ± 0.01 | 0.79 ± 0.03 | PA | 10.18 ± 0.32 | 0.61 ± 0.04 | PA |
| 5c | 3-OMe | 3-OMe—Ph | 1 | Me | H | 7.72 ± 0.13 | 0.59 ± 0.05 | PA | 10.56 ± 0.10 | 0.15 ± 0.01 | ANT |
| 5d | 4-OMe | 3-OMe—Ph | 1 | Me | H | 7.00 ± 0.01 | 0.06 ± 0.03 | ANT | 9.06 ± 0.10 | 0.03 ± 0.01 | ANT |
| 5e | 4-OMe | Ph | 1 | Me | H | 6.11 ± 0.12 | 0.02 ± 0.01 | ANT | 7.56 ± 0.10 | 0.06 ± 0.03 | ANT |
| 5f | 3-Br | Ph | 1 | Me | H | 7.77 ± 0.19 | 0.43 ± 0.04 | PA | 9.70 ± 0.43 | 0.36 ± 0.01 | PA |
| 5g | 3-OMe | β-naphthyl | 1 | Me | H | 6.88 ± 0.07 | 0.17 ± 0.03 | ANT | 9.95 ± 0.64 | −0.20 ± 0.03 | IA |
| 5i | 3-O(CH$_2$)$_4$Ph | Ph | 1 | Me | H | 7.45 ± 0.01 | 0.12 ± 0.02 | ANT | 6.48 ± 0.29 | 0.01 ± 0.01 | ANT |
| 5j | 3-OMe | Me | 1 | Me | H | 9.09 ± 0.10 | 0.95 ± 0.08 | A | 9.19 ± 0.01 | 1.06 ± 0.05 | A |
| 5k | 3-OMe | —CH$_2$Ph | 1 | Me | H | 7.30 ± 0.10 | 0.92 ± 0.06 | A | 9.12 ± 0.05 | 0.31 ± 0.02 | PA |
| 5l | 3-OMe | Ph | 1 | H | H | 8.28 ± 0.01 | 0.84 ± 0.01 | PA | 8.12 ± 0.18 | 0.94 ± 0.03 | A |
| 5m | 3-OMe | Me | 2 | Me | H | 9.08 ± 0.04 | 0.87 ± 0.05 | A | 8.70 ± 0.26 | 1.07 ± 0.06 | A |
| 5n | 3-OMe | Ph | 1 | n-Pr | H | 8.38 ± 0.01 | 1.01 ± 0.04 | A | 9.98 ± 0.26 | 0.73 ± 0.02 | PA |
| 5o | 3-OMe | Ph | 1 | c-Bu | H | 6.48 ± 0.50 | 0.22 ± 0.01 | PA | 8.43 ± 0.40 | 0.29 ± 0.01 | PA |
| 6 | 3-OMe | Ph | 1 | Me | Me | 5.89 ± 0.07 | −0.01 ± 0.03 | ANT | 7.28 ± 0.06 | −0.01 ± 0.03 | ANT |

$^a$pKi values were calculated from IC$_{50}$ values obtained from competition curves by the method of Cheng and Prusoff and are the mean of at least three determinations performed in duplicate.
$^b$The relative intrinsic activity ($IA_r$) values were obtained by dividing the maximal net effect of a test compound by that of MLT.
$^c$A = agonist; PA = partial agonist; ANT = antagonist; IA = Inverse agonist.

In vivo Tests and Animals.

The forced swimming test (FST), Open field Test (OFT) and the in vivo electrophysiology recording were employed to evaluate the anti-depressant activity, the anti-anxiety activity and the sleep promoting properties of the compounds of the present invention [compounds of Formula (I)]. The following results were obtained using compound 5b. Male Sprague-Dawley rats (225-275 g, Charles-River Saint-Constant, Quebec, Canada) were used. The animals were housed at constant room temperature and humidity under a 12 h light/dark cycle. Food and water were available ad libitum. All procedures were approved by local institutional care and use committees and followed the guidelines released by the Canadian Institutes of Health Research.

Forced Swimming Test (FST).

The FST is typically a two-day procedure in which rats are immersed in a water containing cylinder (18 cm in diameter; 40 cm high; water 30 cm deep, 25-27° C.) from which they cannot escape. On the first day, the rats are forced to remain in repeatedly validated and is currently the most popular model for detecting antidepressant activity due to its ease of use, reliability and extremely high predictive validity (Lucki, I. (1997) Behav. Pharmacol. 8(6-7): 523-32).

The FST is carried out according to previously described methods (Page, M. E. et al. Psychopharmacology 165:194-201). At the end of the pre-test, the rats are removed from the water bath, dried with towels and placed in a warm enclosure for 15 min. The rats are then returned to their respective home cages. The cylinders are cleaned and the water replaced between rats. Twenty-four hours later, the rats are re-immersed in the water for the 5 min test. Behavior is recorded continuously throughout the 5 min test by a video camera positioned directly above the water cylinder. Behavioral analysis consists of monitoring, using a computerized Videotrack system (Viewpoint Life Sciences Inc. Qc., Ca) and assigning the predominant behavior to one of the following three categories: i) immobility=rat making minimal movements to keep its head above water; ii)

swimming=actively making swimming movements that cause it to move within the cylinder; and iii) climbing or bursting=forceful thrashing movements with forelimbs against the walls of the cylinder. It has been shown that antidepressants with serotonergic activity selectively increase the occurrence of swimming, whereas those with predominantly noradrenergic activity increase climbing (Lucki, idem). The total time for each type of behavior represents the times that a specified behavior is detected. Animals were randomly assigned to groups that received compound 5b injections (n=6) or vehicle injections (n=6). Injections were administered intraperitoneal (i.p.) three times at 1, 5 and 24 hours prior to the test session (Page et al. idem).

In Vivo Electrophysiology Experiments

Figure 6:
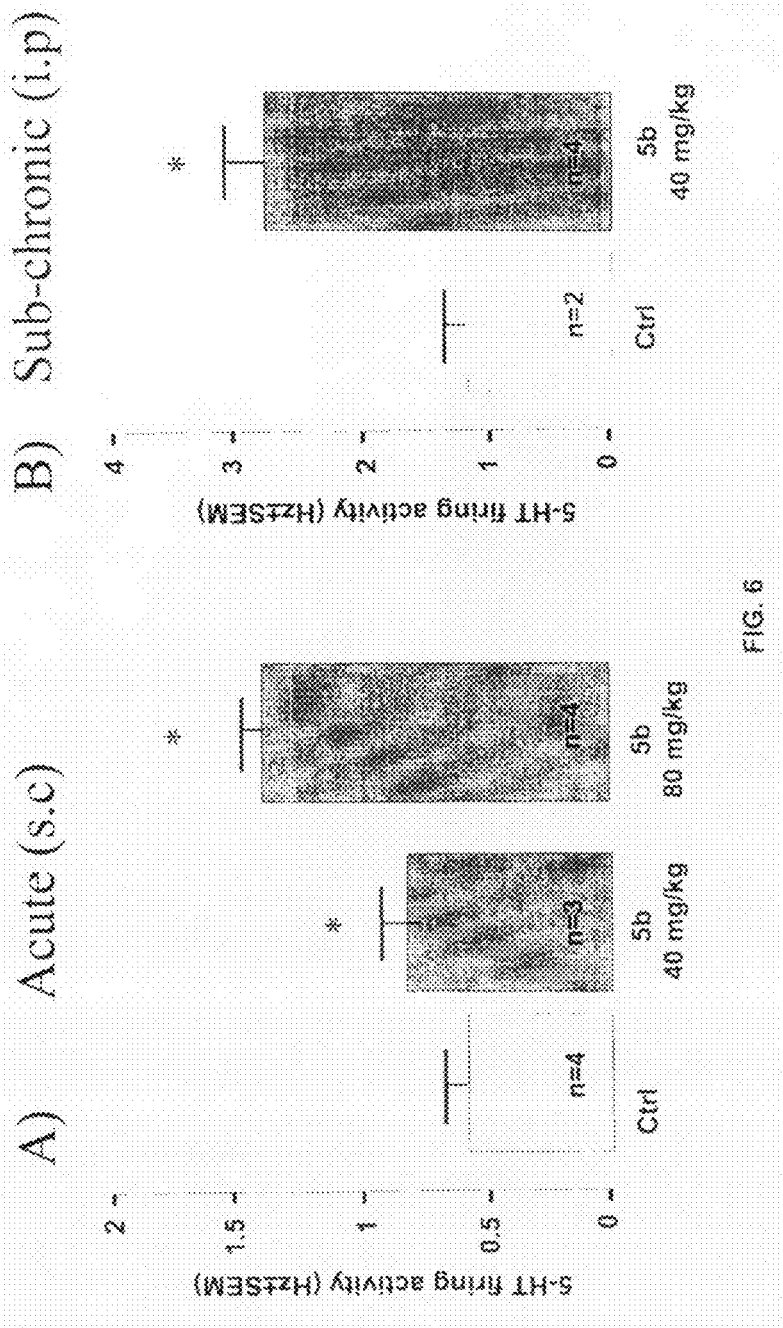
FIG. 6 shows the in vivo electrophysiological recording of 5-HT firing activity. A) Animals were treated with a single injection of compound 5b (40 and 80 mg/kg; subcutaneous) and the 5-HT firing rate recorded. Control animals were treated vehicle (DMSO/saline 7:3). B) Animals (n=4) were sub-chronically treated with compound 5b for 4 days (40 mg/kg, once a day). 5-HT neuronal activity was recorded 24 hours after the last injections. Serotonin neurons of the animals having received compound 5b (n=21) showed a mean firing of 2.80 Hz (SEM±0.4, 133% increase; grey bars). The serotonin neurons of the control animals (n=20) showed a mean firing rate of 1.2 Hz (SEM±0.2; white bars) (*, p<0.001, Student t test).
Figure 7:
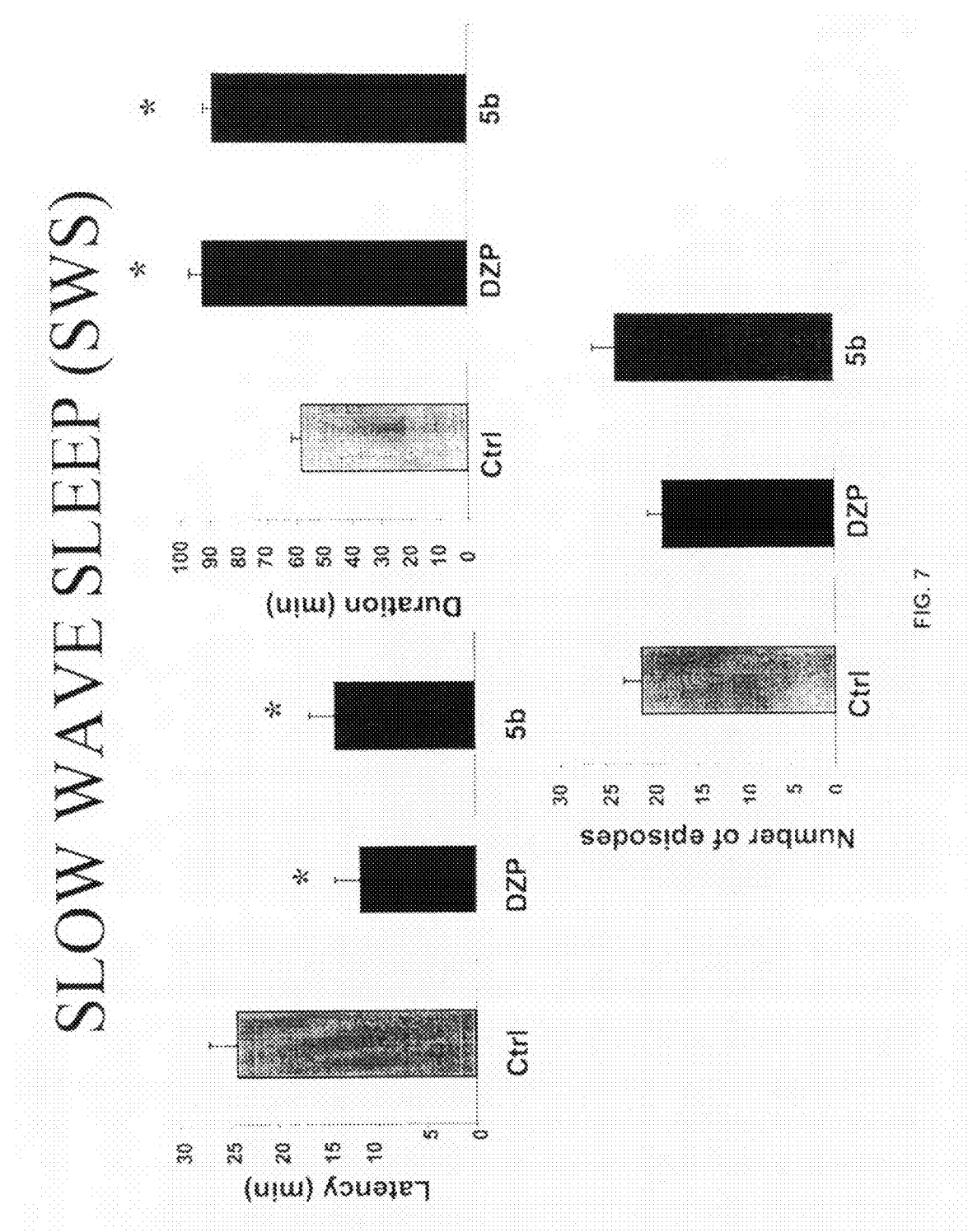
FIG. 7 shows the effects of compound 5b on the Slow Wave Sleep (SWS). The results are expressed as the mean±SEM per n (number) animals tested. All analyses were conducted using Sigma Stats and SPSS software. The significance of the differences between groups was determined by one-way RM analysis of variance (ANOVA) and post-hoc analysis (Animals per group: n=11). Compound 5b was injected subcutaneously 1 minute prior to electroencephalogram (EEG) recording; vehicle (DMSO/saline 7:3) and the anti-anxiety drug diazepam were injected and tested in a similar manner. Latency: Similar to diazepam, compound 5b significantly decreases the latency of SWS. One way RM ANOVA*P<0.05 vs. ctrl. Duration: Similar to diazepam, compound 5b significantly increases the duration of SWS. One way RM ANOVA*P<0.05 vs. ctrl. Number of Episodes: Similar to diazepam, compound 5b has no influence on the number of SWS episodes. One way RM ANOVA*p<0.05 vs. ctrl.
Figure 8:
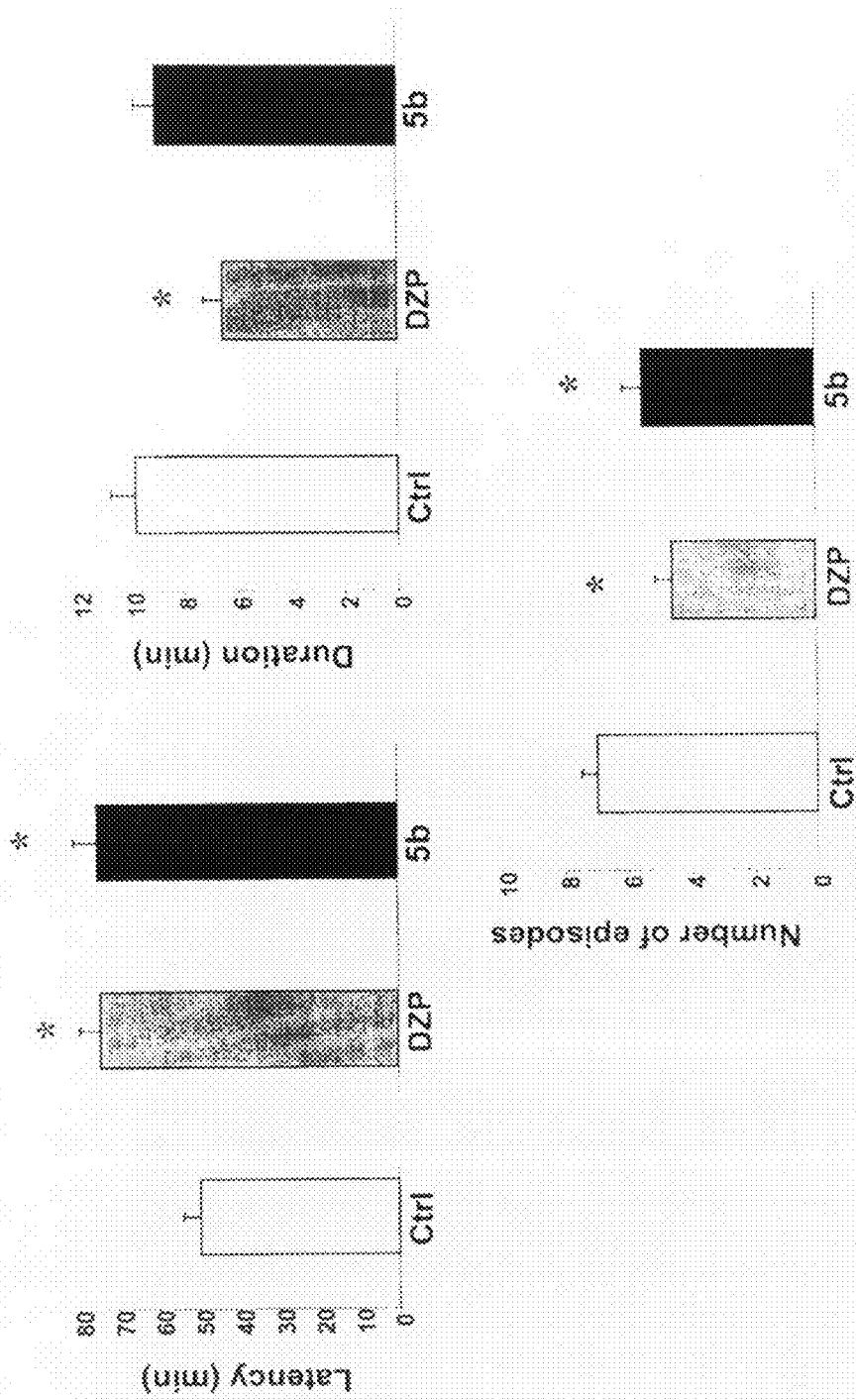
FIG. 8 shows the effects of compound 5b on the Rapid Eye Movement (REM) Sleep. The results are expressed as the mean±SEM per n (number) animals tested. All analyses were conducted using Sigma Stats and SPSS software. The significance of the differences between groups was determined by one-way RM analysis of variance (ANOVA) and post-hoc analysis (Animals per group: 11). Compound 5b was injected subcutaneously 1 minute prior to electroencephalogram (EEG) recording; vehicle and the anti-anxiety drug diazepam were injected and tested in a similar manner. Latency: Similar to diazepam, compound 5b significantly increases the latency of REM sleep. One way RM ANOVA*P<0.05 vs. ctrl. Duration: Contrary to compound 5b, diazepam significantly decreases the duration of REM sleep. One way RM ANOVA*P<0.05 vs. ctrl. Number of Episodes: Similar to diazepam, compound 5b significantly decreases the number of REM sleep episodes. One way RM ANOVA*p<0.05 vs. ctrl.
Figure 9:
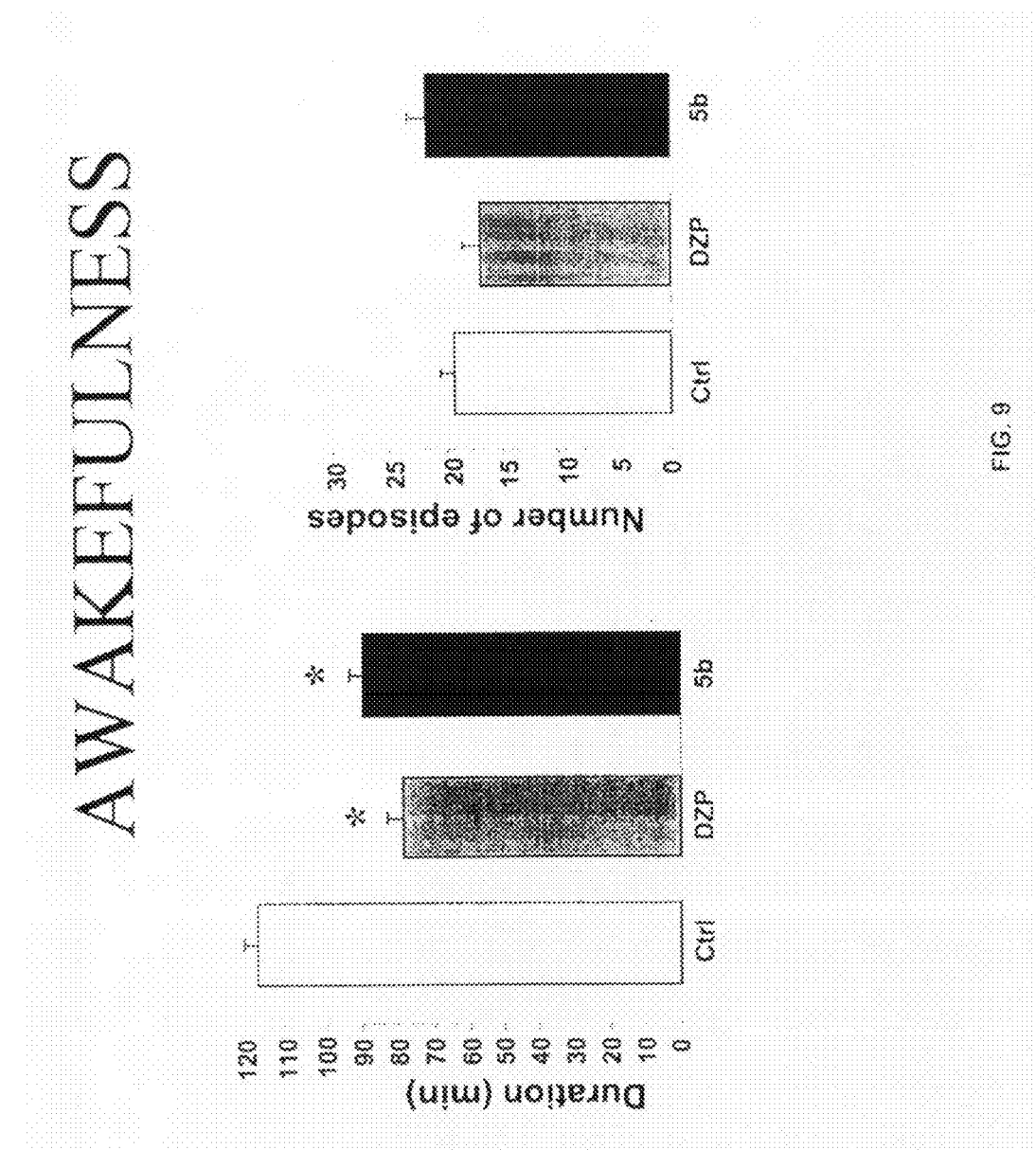
FIG. 9 shows the effects of compound 5b on the Wakefulness. The results are expressed as the mean±SEM per n (number) animals tested. All analyses were conducted using Sigma Stats and SPSS software. The significance of the differences between groups was determined by one-way RM analysis of variance (ANOVA) and post-hoc analysis (Animals per group: 11). Compound 5b was injected subcutaneously 1 minute prior to electroencephalogram (EEG) and electromyogram (EMG) recording; vehicle and the anti-anxiety drug diazepam were injected and tested in a similar manner. Duration: Similar to diazepam, compound 5b significantly decreases the duration of the awake time. Number of Episodes: Similar to diazepam, compound 5b has no influence on the number of awake episodes. One way RM ANOVA*p<0.05 vs. ctrl.
Figure 10:
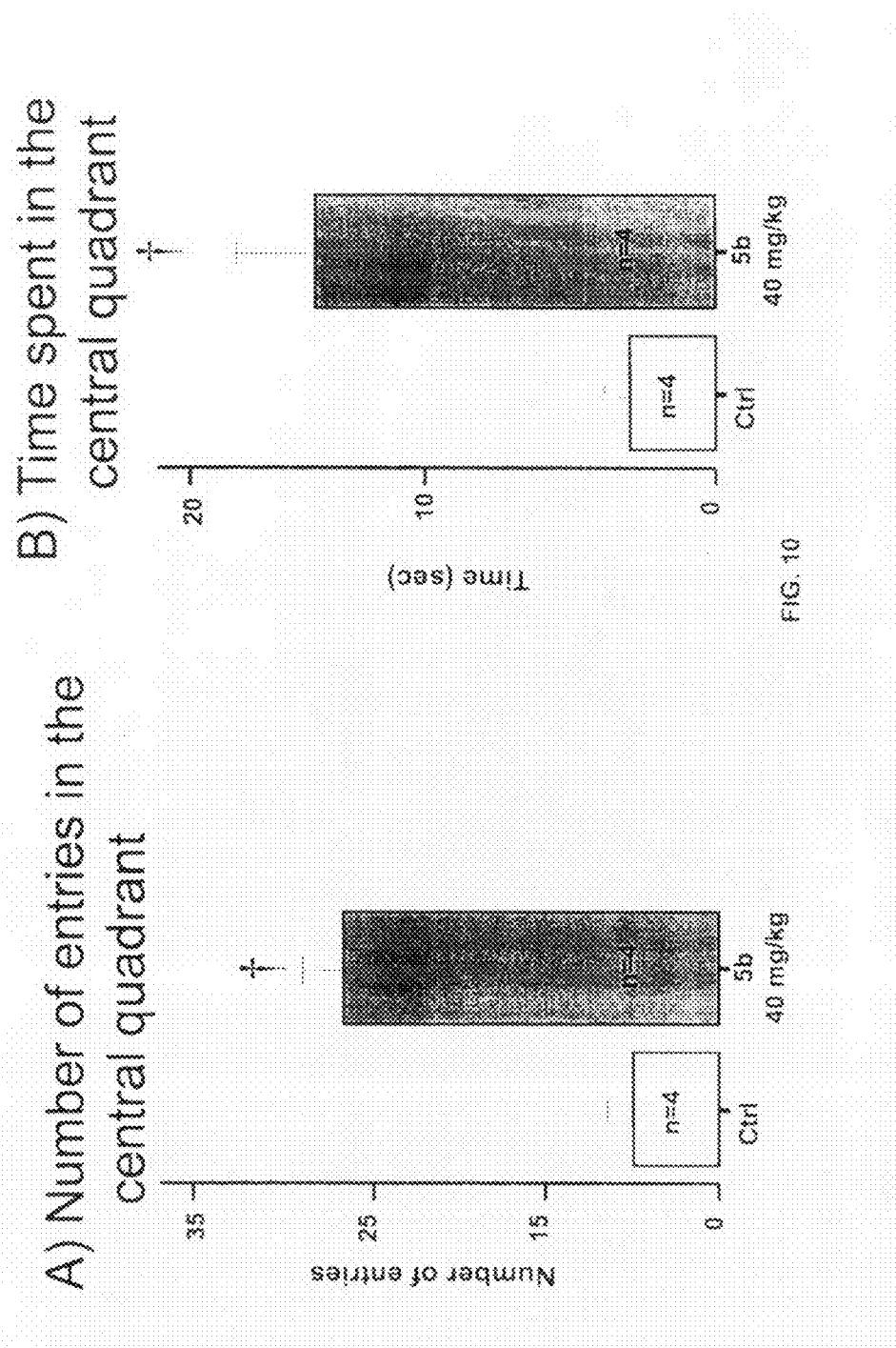
FIG. 10 shows the effects of oral administration of compound 5b on Thigmothaxis as tested in the Open Field Test. Thigmothaxis is an expression of the ratio of time spent in the central area to the time spent in the peripheral area. Compound 5b was orally administered 60 minutes prior to testing. Animals treated with compound 5b (40 mg/kg) displayed an increased number of entries in the central quadrant (A) as well as an increase in the amount of time spent in the central quadrant (B) as compared to animals treated with control (saline cyclodextrin (5%)/DMSO 60:40).

Serotonin (5-HT) neurons are implicated in the regulation of mood (for a review see Gobbi G, (2005) Inter. Rev. Neurobiology 65: 249-271). The increase in serotonergic neurotransmission is linked to the action of antidepressant drugs. For example fluoxetine (Prozac) increases the 5-HT availability by blocking its degradation; mirtazapine (Remeron) increases 5-HT firing activity via an indirect alpha-2 receptor blockade. Consequently, in order to test if compound 5b increases the 5-HT firing activity, in vivo 5-HT neuron activity was recorded after single (40 or 80 mg/kg, subcutaneous) and repeated injections with compound 5b (40 mg/kg, i.p. once a day, for 4 days). For animals treated with a single injection (acute) the recording was done immediately following the injection. For animals treated with repeated injection (sub-chronic) the recording was done 24 hours after the last injection (FIG. 6).

In Vivo Recording of Dorsal Raphe 5-HT Neurons.

Rats (Sprague-Dawley) were anesthetized with chloral hydrate (400 mg/kg i.p.) and placed in a stereotaxic frame (David Kopf Instruments) with the skull positioned horizontally. To maintain a full anesthetic state in which there is no reaction to a tail or paw pinch, chloral hydrate supplements of 100 mg/kg were given as needed. A burr hole was drilled in the midline, 0.9 to 1.2 mm anterior to interaural zero (Paxinos, G. and Watson, C. (1982); The rat brain in Stereotaxic Coordinates; Academy, Sydney). Dorsal raphe was encountered just below the Sylvius aqueduct, 5.0 to 6.5 mm ventral to dura mater. The dorsal raphe 5-HT neurons, in physiological conditions, were identified according to the following criteria: a slow (0.5-2.5 Hz) and regular firing rate; and a long-duration (0.8-1.2 ms) positive action potential (Baraban and Aghajanian (1980) Neuropharmacology 19, 355-363). Neuronal activity was recorded and processed by a computer connected to CED1401 interface-Spike 2 software (Cambridge Electronic Design, Cambridge, UK).

Time of Tests.

All tests as described herein were carried out between 5 PM and 7 PM; electroencephalogram and electromyogram sleep studies were carried between 6 PM to 9 PM.

Antidepressant Properties of Compound 5b.

As illustrated in FIG. 1, repeated administration of 5b in rats (6 animals, 40 mg/kg) significantly decreased the duration of immobility (p<0.05), increased the tendency to swim, and increased the tendency to climb or burst. Since this data corroborates results observed with other anti-depressant drugs, such as the antidepressant selective serotonin reuptake inhibitors (SSRIs) fluoxetine or paroxetine, the tricyclics (TCA) desipramine, imipramine as well as to electroshock (for review see Cryan J F, Valentino R J, Lucki I, Neuroscience and Behavioral Reviews (2005) 29:547-569), it can be concluded that compound 5b has anti-depressant properties.

Open Field Test (OFT).

Exploration and reactivity to a novel open field are assessed in a large rectangular box (100×100 cm). Rats are placed into the center of the open field, and activity is recorded for 5 minutes. Testing took place under bright ambient light conditions to increase the anxiety component of the center areas of the field (defined as the central 60 cm×60 cm portion). The open field comprises two distinct regions; a central and a peripheral region. The ratio between time spent in the central area versus time spent in the peripheral area (i.e. thigmotaxis) is an index of anxiety. The greater the time spent in the central region combined with an increased number of entries in the central region is an indication of the anti-anxiety effect of the compounds of the present invention. A computerized videotrack system (Viewpoint Life Sciences Inc. Qc, Ca) recorded the time of ambulation, the total distance and the time of immobility.

The open field test was carried out using seven (7) male rats (Sprague Dawley) each weighing about 300-340 g. A first group comprising four (4) rats received a gavage administration of vehicle [DMSO (40%)/saline-cyclodextrin 95/5 solution (60%)]. A second group comprising three (3) rats was treated with compound 5b (40 mg/kg). One hour following the administration, the rats were placed in the center of the Open Field apparatus. The duration and number of entries in the center region were recorded over a period of 5 minutes (Table 2).

TABLE 2

| Open Field Test; Thigmothaxis | | | |
|---|---|---|---|
| Entries (#) | | Time in center region (sec) | |
| Ctrl (n = 4) | 5b (40 mg/kg) (n = 3) | Ctrl (n = 4) | 5b (40 mg/kg) (n = 3) |
| 3.75 ± 1.1 | 24.33 ± 4.25 | 3.92 ± 1.2 | 14.5 ± 1.6 |
| t = −5.42, 5 df, p < 0.003 | | t = −5.4, 5 df, p < 0.003 | |

Figure 2:
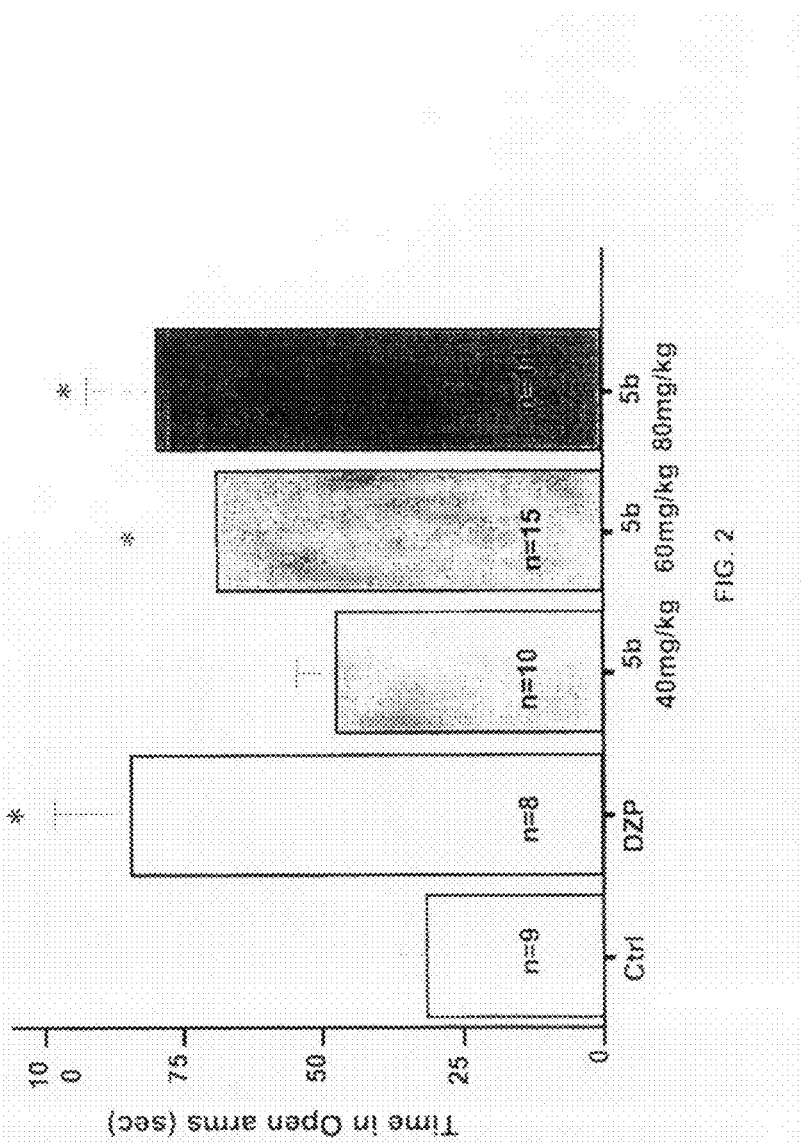
FIG. 2 shows the results obtained with the Elevated Plus Maze Test; a test for measuring anxiety-like behavior. Animals treated with compound 5b (40, 60 and 80 mg/kg; injected 60 min before the test) spent more time in the open arms as evaluated in total time expressed in seconds. Control animals (white bars) are treated with vehicle (DMSO/saline 7:3). Animals treated with the anti-anxiety drug diazepam (DZP) (2 mg/kg; injected 45 min before the test) displayed a similar increase in time spent in the open arms. The results are expressed as the mean±SEM per n (number) animals tested (*, p<0.01, ANOVA or t test).
Figure 3:
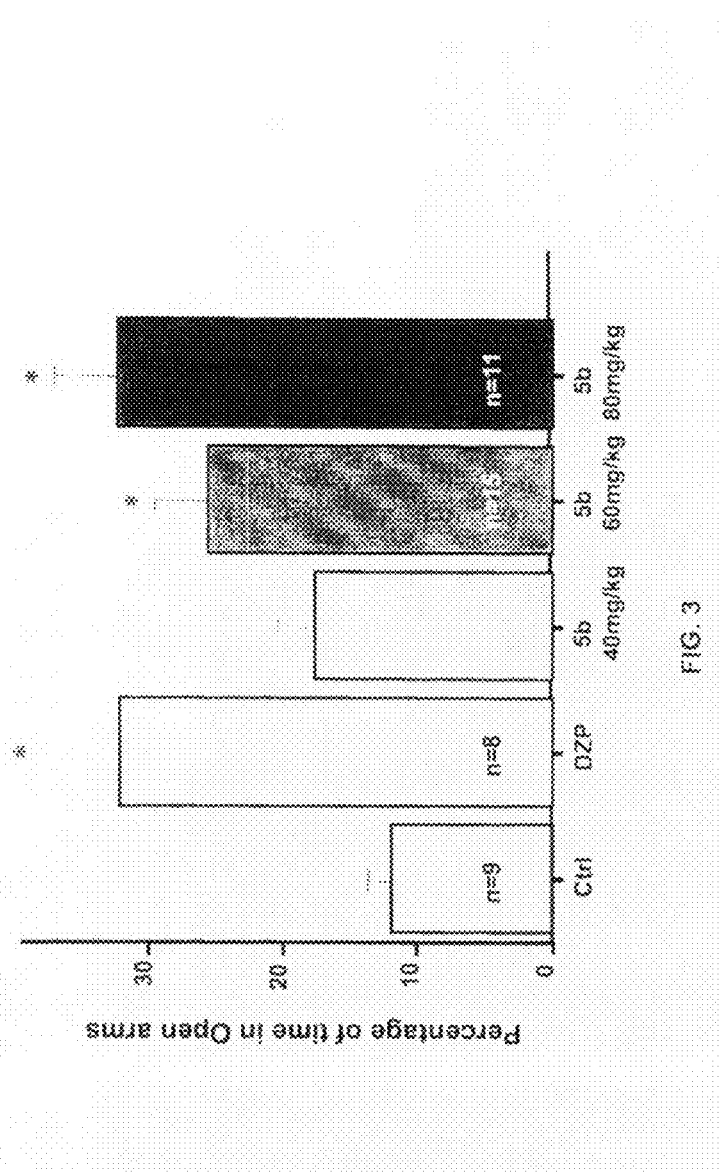
FIG. 3 shows the results obtained with the Elevated Plus Maze Test; a test for measuring anxiety-like behavior. Animals treated with compound 5b (40, 60 and 80 mg/kg; injected 60 min before the test) spent more time in the open arms as evaluated in percentage of time. Control animals (white bars) are treated with vehicle (DMSO/saline 7:3). Animals treated with the anti-anxiety drug diazepam (2 mg/kg; injected 45 min before the test) displayed a similar increase in time spent in the open arms. The results are expressed as the mean±SEM per n (number) animals tested (*, p<0.01, ANOVA or t test).
Figure 4:
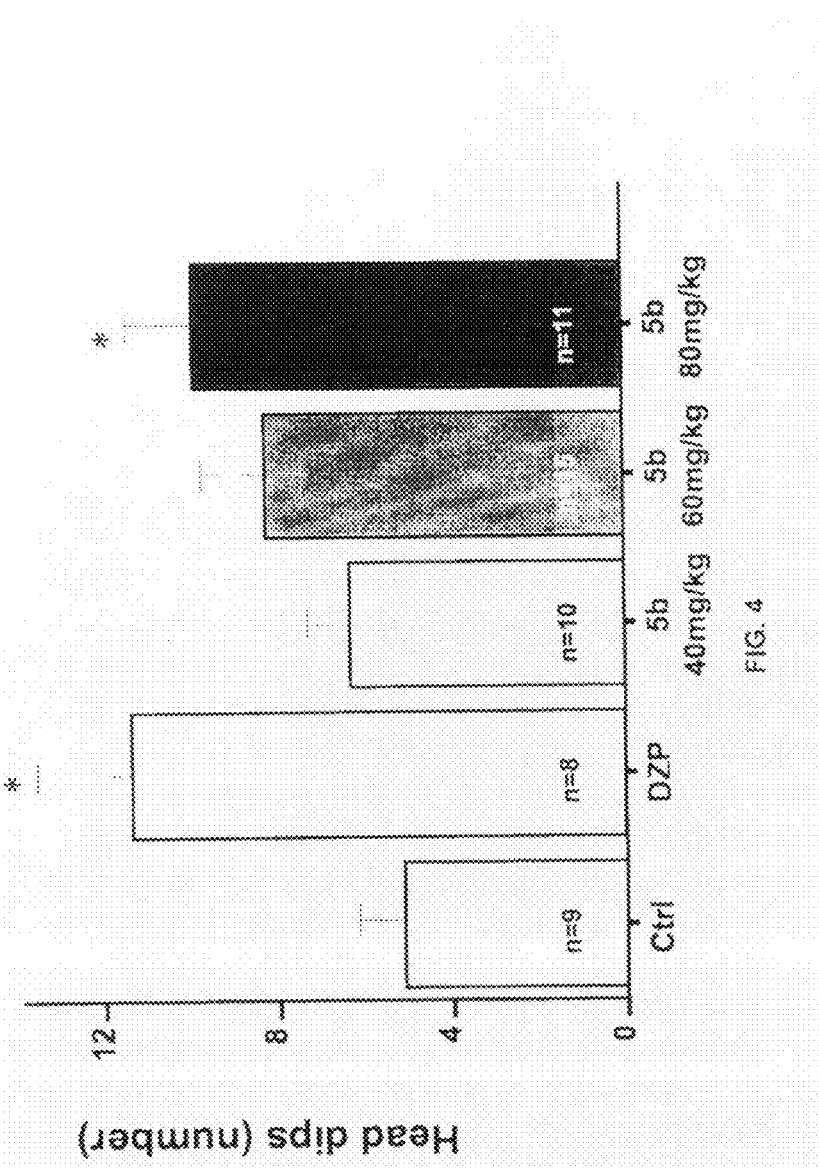
FIG. 4 shows the results obtained with the Elevated Plus Maze Test; a test for measuring anxiety-like behavior. Animals treated with compound 5b (40, 60 and 80 mg/kg; injected 60 min before the test) and animals treated with the anti-anxiety drug diazepam (2 mg/kg; injected 45 min before the test) both displayed an increase in the number of head dips, which is a measure of exploratory behavior and of the anti-anxiety effect of the administered compound. The results are expressed as the mean±SEM per n (number) animals tested (*, p<0.01, ANOVA or t test).
Figure 5:
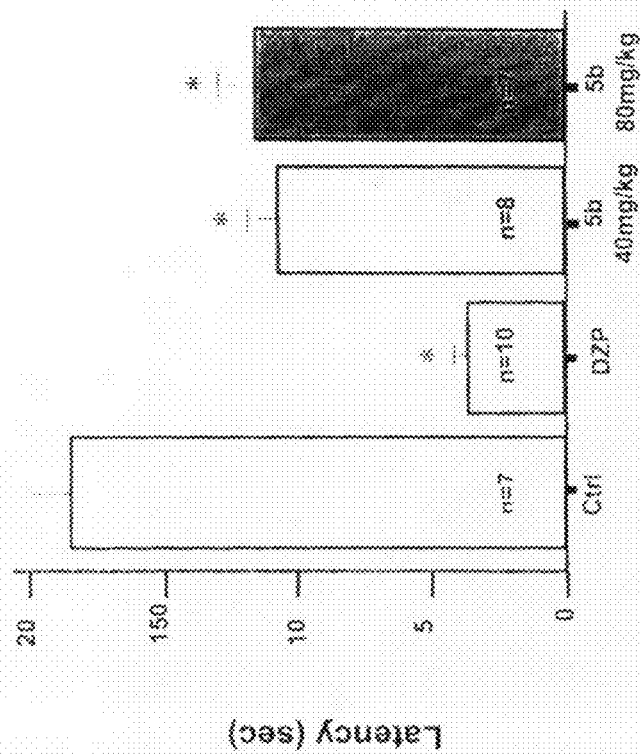
FIG. 5 shows the results obtained with the Novelty-Induced Suppressed Feeding (NSF) Test; a paradigm for measuring anxiety-like behavior. Animals treated with compound 5b (40 and 80 mg/kg; injected 60 min before the test) and animals treated with the anti-anxiety drug diazepam (2 mg/kg; injected 45 min before the test) both displayed a decreased latency to feed, which is a measure of the anti-anxiety effect of the administered compound. Control animals (white bars) are treated with vehicle (DMSO/saline 7:3). The results are expressed as the mean±SEM per n (number) animals tested (44, p<0.01, ANOVA or t test).

The elevated plus maze (EPM) is a validated and reliable test for anxiety (fellow and File, Pharmacol. Biochem Behav. 1986 March; 24(3):525-9). The maze is comprised of two open arms (50×10 cm) and two closed arms (50×10×40 cm) that extend from a common central platform (10×10 cm). The apparatus, made of wood (painted black) was elevated to a height of 80 cm above floor level. The closed arms are located opposite one another. Behavior is recorded over a period of 5 min using a video camera positioned directly above the maze and rated by an observer blind to drug conditions. The major measure of interest is the amount of time spent in the open arms. As an index of general activity and distribution, the total number of entries into both open and closed arms was also recorded. Increased anxiety is defined as a significantly greater preference for the closed arms relative to control animals. In order to increase the sensitivity of this test to anxiolytic activity, tests are carried out under normal room illumination (25 W bulb). Adult Sprague Dawley rats (275 grams) were placed on one of the open arms of the test apparatus and video recorded over a period of 5 minutes in a bright light, sound-attenuated environment. Compound 5b was injected 1 hour prior to testing; the vehicle and Diazepam were injected 45 minutes prior to testing. The behavior was automatically encoded by a computer-based tracking system (Video Track Automated Behavioral Analysis System, Viewpoint Life Science, Inc, Canada) using a power 1401 data acquisition interface (Cambridge Electronic Design, UK). The results are illustrated hereinbelow in Table 3-5 (FIGS. 2-4).

TABLE 3

Anti-anxiety effects of compound 5b.

| | Percentage of time in Open Arms | Total time duration in the Open Arms (sec/open arm) |
|---|---|---|
| Vehicle | 12 ± 1.6 | 31.84 ± 4.8 |
| Diazepam: 2 mg/kg | 32.25 ± 5.9 (P = 0.006)* | 122.0 ± 18.0 (P = 0.008)* |
| Compound 5b: 40 mg/kg | 17.7 ± 2.6 | 47.4 ± 6.86 |
| Compound 5b: 60 mg/kg | 25.5 ± 4.1 (P = 0.02)** | 68.93 ± 11.02 (P = 0.02)** |
| Compound 5b: 80 mg/kg | 31.8 ± 4.8 (P = 0.003)** | 79.16 ± 12.0 (P = 0.001)** |
| Melatonin: 50 mg/kg | 26.67 ± 3.0 (P = 0.001)** | 69.92 ± 7.8 (P = 0.001)** |

*One-way ANOVA test;
**T-test.

TABLE 4

Anti-anxiety effects of compound 5b.

| | Percentage of time in Closed Arms | Total time duration in the Closed Arms (sec/closed arm) |
|---|---|---|
| Vehicle | 88 ± 1.64 | 242.32. ± 6.30 |
| Diazepam: 2 mg/kg | 67.75 ± 5.87 (P = 0.007)* | 178.71 ± 18.16 (P = 0.006)* |
| Compound 5b: 40 mg/kg | 82.30 ± 2.63 | 219.4 ± 9.38 |
| Compound 5b: 60 mg/kg | 74.47 ± 4.06 (P = 0.02)** | 199.83 ± 11.33 (P = 0.01)** |
| Compound 5b: 80 mg/kg | 68.18 ± 4.84 (P = 0.007)** | 181.68 ± 14.32 (P = 0.006)** |
| Melatonin: 50 mg/kg | 73.33 ± 3.02 (P = 0.001)** | 194.42 ± 8.6 (P < 0.001)** |

*One-way ANOVA test;
**T-test.

TABLE 5

Anti-anxiety effects of compound 5b.

| | Head Dips |
|---|---|
| Vehicle | 5.11 ± 0.96 |
| Diazepam: 2 mg/kg | 11.37 ± 2.12 (P = 0.01)** |
| Compound 5b: 40 mg/kg | 6.30 ± 0.98 |
| Compound 5b: 60 mg/kg | 8.27 ± 1.42 |
| Compound 5b: 80 mg/kg | 9.91 ± 1.50 (P = 0.02)** |
| Melatonin: 50 mg/kg | 7.17 ± 0.89 |

**T-test.

Novelty-Induced Suppressed Feeding (NSF) Test.

The NSF test is used to assess the anti-anxiety effect of a drug [Bodnoff et al. Psychopharmacology 1988, 95(3), 298-307]. Sprague Dawley rats were used in the NSF test. The testing apparatus comprises a brightly lit open area covered with lab chow pellets. Forty-eight hours prior to behavioral testing, all food was removed from the apparatus. Animals treated with compound 5b (40 or 80 mg/kg) were injected 60 min before the test, whereas animals treated with vehicle (DMSO/saline 7:3) or diazepam were injected 45 min before the test. The drugs were administered subcutaneously and the experiments were conducted after 5:30 PM. The latency to feed, defined as chewing the food as opposed to merely sniffing or playing with a pellet, was then recorded (Table 6). The experiment was terminated for those animals that had not begun eating within a period of 360 seconds, which animals were assigned a latency score of 360 seconds. All analyses were conducted using Sigma Stats and SPSS software. The results are expressed as the mean±SEM per n (number) animals tested (*, p<0.01, ANOVA or t test).

TABLE 6

Anti-anxiety effects of compound 5b.

| | Latency (sec) |
|---|---|
| Vehicle | 183.86 ± 4.60 |
| Diazepam: 2 mg/kg | 36.10 ± 15.32 (P ≤ 0.001)* |
| Compound 5b: 40 mg/kg | 106.75 ± 10.13 (P ≤ 0.001)* |
| Compound 5b: 80 mg/kg | 115.28 ± 13.89 (P ≤ 0.001)* |

*One-way ANOVA test

Serotonergic Properties of Compound 5b.

As illustrated in FIG. 6, compound 5b, after acute single injection increases the spontaneous activity of 5-HT neurons by 40% (40 mg/kg) and 106% (80 mg/kg) [from 0.66 to 0.93 Hz (40 mg/kg) and from 0.66 to 1.36 Hz (80 mg/kg)]. Sub-chronic treatment (repeated injections, 4 days), increases the spontaneous activity of 5-HT neurons by 133% (from 1.2 Hz to 2.8 Hz). Since this effect was also observed with other classes of antidepressants (Gobbi G and Blier P (2005) Peptides 26: 1383-1393), this result represents a neuronal framework to support the antidepressant and anti-anxiety properties of compound 5b.

Effect of 5b on Slow Wave and Paradoxical (REM) Sleep

Animals

Male rats (Sprague-Dawley) weighing approximately 300-340 g were used for surgical implantation of electroencephalogram (EEG) and electromyogram (EMG) electrodes. Following the recovery from surgery, the animals were housed separately in cages and kept on a 12-hour light/dark cycle (12 h light-12 h dark, 7:30 AM lights on) at a controlled temperature (21° C.). The rats had free access to food and water ad libitum.

Surgery

Rats were anaesthetized using equithesin (425 mg chloral hydrate, 1 ml 100% ethanol, 98 mg pentobarbitone, 213 mg magnesium sulphate and 3 ml propylene glycol, sterile water per 10 ml of solution; 1 ml per 300 g body weight i.p.) and placed in a stereotactic frame. The skull was exposed and carefully cleaned. Two stainless-steel epidural electrodes were implanted for the registration of the EEG under stereotactic control, through 1.5 mm burr holes at the coordinates corresponding to the right parietal-occipital cortex (AP=−2 mm L=3 mm; AP=−7 mm L=3 mm) and the left parietal-occipital cortex (AP=−4.5 mm L=3 mm) according to the atlas by Paxinos (The Rat Brain in Stereotaxic Coordinates, Academic Press, 1995). Three stainless steel wire electrodes, isolated except for the last few millimeters, were implanted into the neck muscles (two bilaterally and one in the middle) for the monitoring of the EMG. The EEG epidural electrodes and the EMG wires were fitted to a six-pin female connector.

For fixation to the skull, the wires and connector were covered with dental acrylic (Coltene/Whaledent Inc. USA). The animals were allowed to recover from the surgery for at least 3-4 days.

Habituation of the Rats to the Room and the 6-Wire Flat

Twenty-four hours (24 h) following the surgery, the rats were placed in the recording room from noon to 9:00 PM, for 3-4 days. The rats were connected to the 6-flat cable (3M), in a freely-moving manner, from 6:00 PM to 9:00 PM for habituation. No recordings were performed at this time, however, the tolerance to the cable and the sleep behavior were observed.

Following 3-4 days of habituation, the rats received the injection of a vehicle (DMSO/saline 7:3, 0.2 ml s.c.) at 6:00 PM and the recording was carried out until 9:00 PM. On the following day the rats received diazepam (2 mg/kg, s.c.) at 6:00 PM and the recording was performed until 9:00 PM. Four days following the injection of diazepam, the rat received 5b (40 mg/kg s.c.) and the recording also performed from 6 to 9 PM.

EEG and EMG Recordings

For each experiment, a rat was placed individually in the cage and monitoring of the signal was carried out via the attachment of a non-restraining 6-wire flat cable and a female connector, which was connected to an impedance transformer with a gain of 10, located above the cage. The EEG signal was amplified (resulting in a total gain of 10,000) and locally filtered. The EMG signal was amplified as the EEG, (EEG: low filter 1.0 Hz; high 1 KHz, EMG: low filter 30.0 Hz; high 3 KHz). The power spectra analysis was performed for identification of the sleep stages. The behavior of the animals was observed during the experiment (eye movements, ambulation, rearing etc.).

Data Analysis

The three classical vigilance-sleep states described in the rat were discriminated on the basis of the cortical EEG and neck EMG, following the classification by Ruigt et al. (*Electroencephalography and clinical Neurophysiology*, 1989, 73: 52-63). Wakefulness was identified by a low-amplitude and desynchronized EEG with sustained EMG activity. Slow wave sleep (SWS, includes Quiet sleep, deep sleep and Pre-REM) was clearly distinguished by high-voltage delta waves (2-4 Hz) and spindles associated with a moderate to high EMG activity. Pre-REM sleep was characterized by a clear theta rhythm in the EEG, frequently alternating with short lasting, high voltage spindles. REM sleep was characterized by a low-amplitude EEG with a pronounced theta rhythm (5.5-8.5 Hz), a complete loss of muscle tone, and a low voltage EMG. In order to avoid transitional periods such as drowsiness, only periods of typical stationary EEG and EMG lasting more than 10 seconds for awake, SWS and REM were considered for analyses. Power spectra of the corresponding EEGs were calculated using the Fast Fourier Transform (FFT) of Spike 2 software.

Effects of Compound 5b on Slow Wave Sleep.

Table 7 shows the characteristics of slow wave sleep (SWS) in 11 rats (indicated as 1-11, in the first column). Compared to a control group, the latency to the onset of the first SWS period was observed to significantly decrease with 5b (40 mg/kg; s.c.). Diazepam (2 mg/kg; s.c.) was also observed to decrease the latency, but not in a significant manner. Compared to a control group, compound 5b and diazepam were observed to also increase the duration of the SWS. Compound 5b and diazepam significantly increase the duration of each SWS episode. However, hardly any effect was observed on the number of SWS episodes with compound 5b. These results are indicative of compound 5b (at a dose of 40 mg/kg) decreasing the latency to the onset of sleep, prolonging the duration of sleep, without changing the SWS sleep architecture.

TABLE 7

Effect of 5b on Slow Wave Sleep.

| | Latency (min) | | |
|---|---|---|---|
| Rat | Ctrl | Diazepam (2 mg/kg) | 5b (40 mg/kg) |
| 1 | 24.16 | 22.5 | 5.05 |
| 2 | 23.09 | 6.51 | 25.12 |
| 3 | 42.72 | 26.36 | 17.24 |
| 4 | 12.46 | 18.02 | 15.73 |
| 5 | 15.81 | 3.98 | 2.73 |
| 6 | 17.57 | 8.25 | 1.05 |
| 7 | 15.13 | 2.86 | 11.9 |
| 8 | 30.61 | 6.93 | 10.85 |
| 9 | 20.6 | 3.06 | 23.2 |
| 10 | 28.69 | 18.42 | 25.9 |
| 11 | 37.08 | 13.59 | 17.62 |
| Mean ± SEM | 24.3 ± 2.8 | 11.8 ± 2.5* | 14.21 ± 2.6* |

ONE WAY RM ANOVA F = (2.20): 9.07,
$p < 0.002$;
*$p < 0.05$ vs. Ctrl

| | Duration (min) | | |
|---|---|---|---|
| Rat | Ctrl | Diazepam (2 mg/kg) | 5b (40 mg/kg) |
| 1 | 38.94 | 58.45 | 110.29 |
| 2 | 67.02 | 89.15 | 73.51 |
| 3 | 51.13 | 84 | 87.14 |
| 4 | 63.01 | 105.18 | 92.65 |
| 5 | 52.76 | 99.03 | 89.42 |
| 6 | 67.01 | 103.14 | 80.00 |
| 7 | 51.78 | 92.36 | 88.47 |
| 8 | 79.6 | 114.55 | 79.1 |
| 9 | 51.7 | 94.85 | 85.8 |
| 10 | 60.58 | 88.22 | 80.84 |
| 11 | 55.62 | 83.9 | 104.2 |
| Mean ± SEM | 58.1 ± 3.2 | 92.0 ± 4.4* | 88.3 ± 3.2* |

ONE WAY RM ANOVA F = (2.20): 22.3,
$p < 0.001$;
*$p < 0.05$ vs. Ctrl

| | Number (episodes) | | |
|---|---|---|---|
| Rat | Ctrl | Diazepam (2 mg/kg) | 5b (40 mg/kg) |
| 1 | 9 | 9 | 22 |
| 2 | 25 | 12 | 29 |
| 3 | 32 | 27 | 29 |
| 4 | 13 | 19 | 28 |
| 5 | 25 | 23 | 26 |
| 6 | 25 | 20 | 19 |
| 7 | 21 | 21 | 34 |
| 8 | 25 | 23 | 35 |
| 9 | 21 | 14 | 14 |
| 10 | 22 | 17 | 11 |
| 11 | 15 | 13 | 14 |
| Mean ± SEM | 21.1 ± 1.9 | 18.0 ± 1.6 | 23.7 ± 2.5 |

ONE WAY RM ANOVA F = (2.20): 3.4,
$p < 0.053$ NS

| | Mean of a Single Episode (min) | | |
|---|---|---|---|
| Rat | Ctrl | Diazepam (2 mg/kg) | 5b (40 mg/kg) |
| 1 | 4.32 | 6.49 | 5.01 |
| 2 | 2.68 | 7.42 | 2.53 |

TABLE 7-continued

| | | | |
|---|---|---|---|
| 3 | 1.59 | 3.11 | 3 |
| 4 | 4.84 | 5.53 | 3.3 |
| 5 | 2.11 | 4.3 | 3.43 |
| 6 | 2.68 | 5.15 | 4.21 |
| 7 | 2.46 | 4.39 | 2.6 |
| 8 | 3.18 | 4.98 | 2.26 |
| 9 | 1.03 | 6.77 | 6.12 |
| 10 | 2.75 | 5.18 | 7.34 |
| 11 | 3.7 | 6.45 | 7.44 |
| Mean ± SEM | 2.8 ± 0.33 | 5.4 ± 0.38* | 4.3 ± 0.57* |

ONE WAY RM ANOVA F = (2.20): 10.6,
$p < 0.001$;
*$p < 0.05$ vs. Ctrl

Effects of Compound 5b on REM Sleep.

Table 8 shows the characteristics of REM sleep in 11 rats (indicated as 1-11, in the first column). Compared to a control group, the latency to the onset of the first REM sleep period was observed to significantly increase with 5b (40 mg/kg; s.c.) and diazepam. However, hardly any effect was observed on the duration, the number of REM sleep episodes and the mean duration of a single REM episode with compound 5b. Since it has been observed that stressed or depressive-like rats have a reduced latency to the onset of the REM sleep period (Cheeta et al., 1997. *Biol Psychiatry* 41: 419-427), the data showing that 5b increases the onset of the first REM episode, suggests that it could be a good sleep-inducer. More importantly, in people suffering from major depression, typically displaying reduced slow wave sleep, an early onset of the first episode of REM sleep, and an increased phasic REM sleep (Thase, M. E. 1998. *J. Clin. Psychiatry* 59: Suppl. 4:55-65), the administration of compound 5b results in decreased latency to SWS, increased amount of total SWS and increased latency to the first episode of REM sleep. These results are indicative of compound 5b having a pharmacological profile as a drug for treating patients suffering from depression and insomnia.

TABLE 8

Effect of 5b on REM Sleep.

| | Latency (min) | | |
|---|---|---|---|
| Rat | Ctrl | Diazepam (2 mg/kg) | 5b (40 mg/kg) |
| 1 | 33.37 | 58.92 | 80.26 |
| 2 | 36.66 | 73.3 | 54.26 |
| 3 | 54.48 | 61.33 | 43.83 |
| 4 | 65.83 | 102.43 | 76.1 |
| 5 | 46.99 | 56.83 | 62.31 |
| 6 | 49.09 | 56.59 | 60.92 |
| 7 | 59.58 | 96.4 | 109.5 |
| 8 | 54.22 | 61.69 | 86.49 |
| 9 | 37.5 | 93.4 | 71.16 |
| 10 | 33.71 | 72.26 | 80.13 |
| 11 | 75.34 | 86.41 | 101.41 |
| Mean ± SEM | 49.7 ± 4.1 | 74.5 ± 5.2* | 75.1 ± 5.9* |

ONE WAY RM ANOVA F = (2.20): 14.1,
$p < 0.001$;
*$p < 0.05$ vs. Ctrl

| | Duration (min) | | |
|---|---|---|---|
| Rat | Ctrl | Diazepam (2 mg/kg) | 5b (40 mg/kg) |
| 1 | 7.33 | 6.04 | 8.66 |
| 2 | 11.01 | 5.45 | 7.04 |
| 3 | 14.22 | 12.03 | 13.89 |
| 4 | 7.02 | 5.18 | 4.96 |
| 5 | 8.83 | 7.71 | 8.51 |
| 6 | 12.96 | 8.81 | 11.6 |
| 7 | 6.25 | 4.23 | 5.61 |

TABLE 8-continued

| | | | |
|---|---|---|---|
| 8 | 7.87 | 5.86 | 7.2 |
| 9 | 5.9 | 2.55 | 11.18 |
| 10 | 13.38 | 8.52 | 11.76 |
| 11 | 13.82 | 5.62 | 9.48 |
| Mean ± SEM | 9.8 ± 0.9 | 6.5 ± 0.7* | 9.0 ± 0.8** |

ONE WAY RM ANOVA F = (2.20): 11.7,
$p < 0.001$;
*$p < 0.05$ vs. Ctrl;
**$p < 0.05$ vs. diazepam

| | Number (episodes) | | |
|---|---|---|---|
| Rat | Ctrl | Diazepam (2 mg/kg) | 5b (40 mg/kg) |
| 1 | 4 | 4 | 7 |
| 2 | 7 | 3 | 4 |
| 3 | 10 | 7 | 9 |
| 4 | 3 | 4 | 3 |
| 5 | 7 | 5 | 8 |
| 6 | 8 | 9 | 6 |
| 7 | 8 | 4 | 4 |
| 8 | 7 | 4 | 3 |
| 9 | 7 | 3 | 5 |
| 10 | 8 | 4 | 7 |
| 11 | 8 | 4 | 5 |
| Mean ± SEM | 7.0 ± 0.5 | 4.6 ± 0.5* | 5.5 ± 0.6 |

ONE WAY RM ANOVA F = (2.20): 7.3,
$p < 0.004$;
*$p < 0.05$ vs. Ctrl;

| | Mean of a Single Episode (min) | | |
|---|---|---|---|
| Rat | Ctrl | Diazepam (2 mg/kg) | 5b (40 mg/kg) |
| 1 | 1.8325 | 1.51 | 1.237 |
| 2 | 1.572 | 1.816 | 1.76 |
| 3 | 1.422 | 1.718 | 1.54 |
| 4 | 2.34 | 1.295 | 1.65 |
| 5 | 1.261 | 1.542 | 1.063 |
| 6 | 1.62 | 0.978 | 1.933 |
| 7 | 0.781 | 1.05 | 1.402 |
| 8 | 1.124 | 1.465 | 2.4 |
| 9 | 0.842 | 0.85 | 2.23 |
| 10 | 1.67 | 2.13 | 1.68 |
| 11 | 2.352 | 1.405 | 1.896 |
| Mean ± SEM | 1.53 ± 0.15 | 1.43 ± 0.11 | 1.7 ± 0.12 |

ONE WAY RM ANOVA F = (2.20): 1.4,
$p < 0.3$ NS

Effects of Compound 5b on Wakefulness.

Table 9 shows the characteristics of the Awake Time in 11 rats (indicated as 1-11, in the first column). Compared to a control group, 5b (40 mg/kg; s.c.) and diazepam significantly decreased the duration of the Awake Time. However, hardly any effect was observed on the number of Awake Time episodes and the mean duration of a single Awake Time episode with compound 5b.

TABLE 9

Effect of 5b on Wakefulness.

| | Duration (min) | | |
|---|---|---|---|
| Rat | Ctrl | Diazepam (2 mg/kg) | 5b (40 mg/kg) |
| 1 | 133.7 | 115.52 | 61.05 |
| 2 | 100.91 | 71.04 | 92.11 |
| 3 | 114.65 | 80.79 | 78.94 |
| 4 | 109.97 | 69.58 | 82.38 |
| 5 | 118.36 | 73.27 | 82.05 |
| 6 | 99.99 | 68.04 | 88.37 |
| 7 | 120.28 | 83.4 | 85.99 |
| 8 | 92.55 | 62.00 | 93.61 |
| 9 | 122.35 | 82.58 | 83.69 |
| 10 | 106.06 | 85.76 | 87.41 |

TABLE 9-continued

| | 11 | 110.57 | 66.32 | 90.48 |
|---|---|---|---|---|
| | Mean ± SEM | 111.7 ± 3.54 | 78.2 ± 4.43* | 84.1 ± 2.68* |

ONE WAY RM ANOVA F = (2.20): 21.4,
p < 0.00001;
*p < 0.05 vs. Ctrl

| | Number (episodes) | | |
|---|---|---|---|
| Rat | Ctrl | Diazepam (2 mg/kg) | 5b (40 mg/kg) |
| 1 | 9.00 | 9 | 18 |
| 2 | 23 | 12 | 26 |
| 3 | 30 | 20 | 24 |
| 4 | 13 | 19 | 28 |
| 5 | 24 | 24 | 23 |
| 6 | 23 | 17 | 18 |
| 7 | 16 | 22 | 36 |
| 8 | 23 | 23 | 34 |
| 9 | 21 | 15 | 13 |
| 10 | 22 | 15 | 6 |
| 11 | 12 | 11 | 12 |
| Mean ± SEM | 19.6 ± 1.89 | 17.0 ± 1.52 | 21.6 ± 2.8 |

ONE WAY RM ANOVA F = (2.20): 1.73,
p < 0.2 NS

| | Mean of a Single Episode (min) | | |
|---|---|---|---|
| Rat | Ctrl | Diazepam (2 mg/kg) | 5b (40 mg/kg) |
| 1 | 14.85 | 12.83 | 3.39 |
| 2 | 4.38 | 5.92 | 3.54 |
| 3 | 3.82 | 4.03 | 3.28 |
| 4 | 8.45 | 3.66 | 2.94 |
| 5 | 4.93 | 3.05 | 3.56 |
| 6 | 4.34 | 4.00 | 4.9 |
| 7 | 7.51 | 3.79 | 2.38 |
| 8 | 4.02 | 2.69 | 2.75 |
| 9 | 5.82 | 5.5 | 6.43 |
| 10 | 4.82 | 5.71 | 14.56 |
| 11 | 9.21 | 6.02 | 7.54 |
| Mean ± SEM | 6.5 ± 1.0 | 2.7 ± 0.84 | 3.54 ± 1.06 |

ONE WAY RM ANOVA F = (2.20): 0.96,
p < 0.3 NS

It is to be understood that the invention is not limited in its application to the details of construction and parts illustrated in the accompanying drawings and described hereinabove. The invention is capable of other embodiments and of being practiced in various ways. It is also understood that the phraseology or terminology used herein is for the purpose of description and not limitation. Hence, although the present invention has been described hereinabove by way of preferred embodiments thereof, it can be modified, without departing from the spirit, scope and nature of the subject invention as defined in the appended claims.

What is claimed is:

1. A composition comprising a compound of Formula I and a pharmaceutically acceptable excipient, wherein said composition is formulated for oral, transdermal, or parenteral administration, and wherein Formula I is

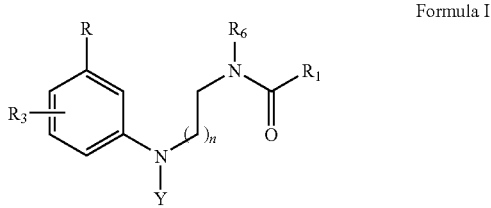

Formula I or a pharmaceutically acceptable salt thereof, wherein:
a) n is 1 or 2;
b) m is 0, 1 or 2;
c) p is 0, 1, 2, 3, 4, 5, 6, 7 or 8;
d) v is 2 or 3;
e) A is aryl or heteroaryl;
f) Z is O, S or $NR_8$;
g) Y is selected from the group consisting of hydrogen, aryl, heteroaryl, $C_2$-$C_6$ alkyl, $C_3$-$C_6$ cycloalkyl, and

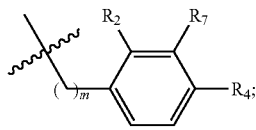

h) R is selected from the group consisting of hydrogen, hydroxyl, —$OCF_3$, $CF_3$, $C_1$-$C_8$ alkyl, $C_1$-$C_8$ alkyloxy, $C_1$-$C_8$ alkylthio, halogen and —Z—$(CH_2)_p$-A;
i) $R_1$ is selected from the group consisting of $C_1$-$C_3$ alkyl, $C_3$-$C_6$ cycloalkyl, $CF_3$, hydroxy-substituted $C_1$-$C_4$ alkyl, hydroxy-substituted $C_3$-$C_6$ cycloalkyl, and $NHR_5$, wherein $R_5$ is $C_1$-$C_3$ alkyl or $C_3$-$C_6$ cycloalkyl;
j) $R_2$ is selected from the group consisting of: hydrogen, $C_1$-$C_4$ alkyl, $C_1$-$C_4$ alkyloxy, $OCF_3$, $CF_3$, hydroxyl, and halogen;
k) $R_3$ is selected from the group consisting of $C_2$-$C_4$ alkyl, $C_1$-$C_4$ alkyloxy, $OCF_3$, $CF_3$, hydroxyl, F, Br, and I;
l) R and $R_3$ may be connected together to form an —O—$(CH_2)_v$ bridge representing with the carbon atoms to which they are attached a 5- or 6-membered heterocyclic ring system;
m) $R_4$ is selected from the group consisting of hydrogen, $C_1$-$C_4$ alkyl, $C_1$-$C_4$ alkyloxy, $OCF_3$, $CF_3$, hydroxyl, and halogen;
n) $R_6$ is selected from the group consisting of hydrogen and $C_1$-$C_6$ alkyl;
o) $R_7$ is selected from the group consisting of hydrogen, $C_1$-$C_4$ alkyl, $C_1$-$C_4$ alkyloxy, $OCF_3$, $CF_3$, hydroxyl, and halogen; and
p) $R_8$ is selected from the group consisting of hydrogen and $C_1$-$C_4$ alkyl, with the proviso that when
  a) Y is $CH_3$, then R is OMe, OBu, OHex or $O(CH_2)_4Ph$, $R_1$ is $CH_3$, and $R_6$ is H, with the further proviso that when R is OMe then n is 2;
  b) $R_3$ is hydrogen, then R is hydrogen, OMe, Br, OBu, OHex or $O(CH_2)_4Ph$, with the further proviso that when:
    i) R is hydrogen, then Y is Ph, n is 1, $R_6$ is H and $R_1$ is $CH_3$;
    ii) R is OMe, then Y is Ph, n is 1, $R_6$ is H and $R_1$ is $CH_3$;
    iii) R is OMe, then Y is 3-MeOPh, n is 1, $R_6$ is H and $R_1$ is $CH_3$;
    iv) R is Br, then Y is Ph, n is 1, $R_6$ is H and $R_1$ is $CH_3$;
    v) R is OMe, then Y is β-naphthyl; n is 1, $R_6$ is H and $R_1$ is $CH_3$;
    vi) R is $O(CH_2)_4Ph$, then Y is Ph, n is 1, $R_6$ is H and $R_1$ is $CH_3$;
    vii) R is OMe, then Y is $CH_2Ph$; n is 1, $R_6$ is H and $R_1$ is $CH_3$;

ix) R is OMe, then Y is Ph; n is 1, $R_6$ is H and $R_1$ is Pr;
x) R is OMe, then Y is Ph; n is 1, $R_6$ is H and $R_1$ is c-Bu; and
xi) R is OMe, then Y is Ph; n is 1, $R_6$ is Me and $R_1$ is $CH_3$; and c) Y is Et, then R cannot be H, $CH_3$, OMe or Et,
wherein the compound of Formula I does not have structures where:

R is OMe, $R_3$ is H, Y is H, n is 1, $R_6$ is H, and $R_1$ is $CH_3$; and
R is H, $R_3$ is OMe, Y is H, n is 1, $R_6$ is H, and $R_1$ is $CH_3$, and
wherein the compound has antidepressant activity or sleep inducing properties.

2. The composition of claim 1 being a ligand to MLT receptor subtypes $MT_1$ and/or $MT_2$.

3. The composition of claim 2, wherein:
a) n is 1 or 2;
b) m is 0, or 1;
c) p is 0, 1, 2, 3, or 4;
d) A is phenyl;
e) Z is O;
f) Y is selected from the group consisting of hydrogen, β-naphthyl, thiophene-2-yl, and

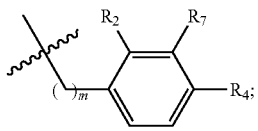

g) R is selected from the group consisting of hydrogen, methoxy, Br and $-Z-(CH_2)_p-A$;
h) $R_1$ is selected from the group consisting of methyl, propyl and cyclobutyl;
i) $R_2$ is hydrogen;
j) $R_3$ is selected from the group consisting of Br and methoxy;
k) $R_4$ is hydrogen;
l) $R_6$ is hydrogen or methyl; and
m) $R_7$ is hydrogen or methoxy.

4. The composition of claim 3, wherein the compound is selected from the group consisting of N-{2-[(3-Methoxyphenyl)-phenylamino]ethyl}acetamide, N-[2-(bis-3-methoxyphenylamino)ethyl]acetamide, N-{2-[(4-Methoxyphenyl)-3-methoxyphenylamino]ethyl}acetamide, N-{2-[(4-Methoxyphenyl)-phenylamino]ethyl}acetamide, N-{2-[(3-bromophenyl)-phenylamino]ethyl}acetamide, N-{2-[(3-Methoxyphenyl)-β-naphthylamino]ethyl}acetamide, N-{2-[(3-Methoxyphenyl)-benzylamino]ethyl}acetamide, N-{2-[(3-Methoxyphenyl)-amino]ethyl}acetamide, N-{2-[(3-Methoxyphenyl)-phenylamino]ethyl}butanamide, N-{2-[(3-Methoxyphenyl)-phenylamino]ethyl}cyclobutancarboxamide, and N-Methyl-N-{2-[(3-methoxyphenyl)-phenylamino]ethyl}acetamide.

5. The composition of claim 4, wherein the compound is N-{2-[(3-Methoxyphenyl)-phenylamino]ethyl}acetamide.

6. The composition of claim 1, comprising from about 0.1% to about 99% by weight of the compound of Formula I.

7. The composition of claim 6, comprising from about 10% to about 60% by weight of the compound of Formula I.

8. A method of interacting with the $MT_1$ and/or $MT_2$ MLT receptor subtypes comprising administering to a subject in need thereof an effective amount of a composition of claim 1.

9. The method of claim 8, wherein the compound of Formula I is a ligand to MLT receptor subtypes $MT_1$ and/or $MT_2$.

10. The method of claim 9, wherein the interacting treats conditions mediated by the $MT_1$ and/or $MT_2$ receptor.

11. The method of claim 10, wherein the condition is selected from the group consisting of sleep disorders, anxiety, depression, and chronobiological disorders.

12. The method of claim 11, wherein the condition is sleep disorders.

13. The method of claim 12, wherein the compound is selected from the group consisting of N-{2-[(3-Methoxyphenyl)-phenylamino]ethyl}acetamide, N-[2-(bis-3-methoxyphenylamino)ethyl]acetamide, N-{2-[(4-Methoxyphenyl)-3-methoxyphenylamino]ethyl}acetamide, N-{2-[(4-Methoxyphenyl)-phenylamino]ethyl}acetamide, N-{2-[(3-bromophenyl)-phenylamino]ethyl}acetamide, N-{2-[(3-Methoxyphenyl)-β-naphthylamino]ethyl}acetamide, N-{2-[(3-Methoxyphenyl)-benzylamino]ethyl}acetamide, N-{2-[(3-Methoxyphenyl)-amino]ethyl}acetamide, N-{2-[(3-Methoxyphenyl)-phenylamino]ethyl}butanamide, N-{2-[(3-Methoxyphenyl)-phenylamino]ethyl}cyclobutancarboxamide, and N-Methyl-N-{2-[(3-methoxyphenyl)-phenylamino]ethyl}acetamide.

14. The method of claim 13, wherein the compound is N-{2-[(3-Methoxyphenyl)-phenylamino]ethyl}acetamide.

15. A compound of Formula:

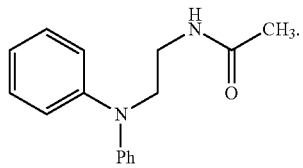 [SMILES: CC(=O)NCCN(c1ccccc1)c1ccccc1]

16. A compound of Formula:

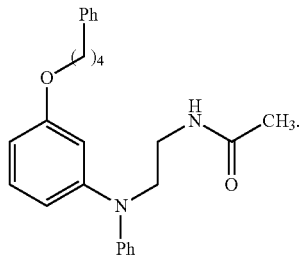

17. A compound of Formula:

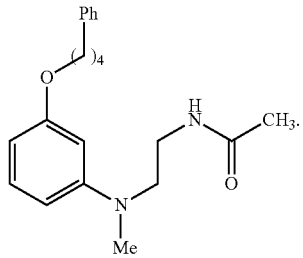

18. A compound of Formula:

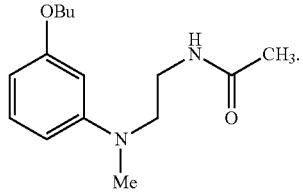

19. A compound of Formula:

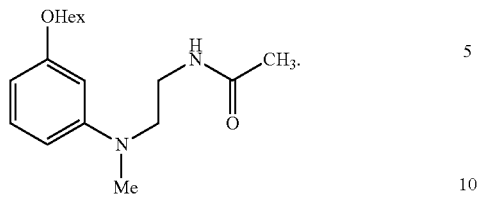

20. The composition of claim 1, wherein the composition is formulated for oral administration.

21. The composition of claim 20, wherein the composition is a tablet, capsule, or a granule.

22. The composition of claim 20, wherein the composition is a liquid solution or suspension.

23. The composition of claim 1, wherein the composition is formulated for transdermal administration.

24. The composition of claim 23, wherein the composition is comprised in a dermal or skin patch.

25. The composition of claim 1, wherein the composition is formulated for parenteral administration.

26. The composition of claim 25, wherein parenteral administration is intramuscular, intravenous, or subcutaneous administration.

* * * * *